United States Patent
van der Poll et al.

(10) Patent No.: US 10,881,745 B2
(45) Date of Patent: Jan. 5, 2021

(54) FORMULATION OF NANOSTRUCTURED GELS FOR INCREASED AGENT LOADING AND ADHESION

(71) Applicant: Alivio Therapeutics, Inc., Boston, MA (US)

(72) Inventors: Derek G. van der Poll, Medford, MA (US); Dominick J. Blasioli, Chelmsford, MA (US); Gregory T. Zugates, Chelmsford, MA (US)

(73) Assignee: ALIVIO THERAPEUTICS, INC., Boston, MA (US)

(*) Notice: Subject to any disclaimer, the term of this patent is extended or adjusted under 35 U.S.C. 154(b) by 0 days.

(21) Appl. No.: 15/974,535

(22) Filed: May 8, 2018

(65) Prior Publication Data

US 2018/0318442 A1 Nov. 8, 2018

Related U.S. Application Data

(60) Provisional application No. 62/502,872, filed on May 8, 2017.

(51) Int. Cl.
| | | |
|---|---|---|
| *A61P 23/00* | (2006.01) | |
| *A61P 29/00* | (2006.01) | |
| *A61L 27/52* | (2006.01) | |
| *A61L 27/54* | (2006.01) | |
| *A61K 9/00* | (2006.01) | |
| *A61K 9/19* | (2006.01) | |
| *A61K 9/14* | (2006.01) | |
| *A61K 47/10* | (2017.01) | |
| *A61K 47/69* | (2017.01) | |
| *A61K 47/14* | (2017.01) | |
| *A61K 47/26* | (2006.01) | |
| *A61K 31/445* | (2006.01) | |
| *A61K 31/245* | (2006.01) | |
| *A61K 31/47* | (2006.01) | |
| *A61K 31/167* | (2006.01) | |
| *A61K 47/22* | (2006.01) | |
| *A61K 47/02* | (2006.01) | |
| *A61K 9/06* | (2006.01) | |
| *A61K 47/20* | (2006.01) | |

(52) U.S. Cl.
CPC .......... *A61K 47/6903* (2017.08); *A61K 9/06* (2013.01); *A61K 31/167* (2013.01); *A61K 31/245* (2013.01); *A61K 31/445* (2013.01); *A61K 31/47* (2013.01); *A61K 47/02* (2013.01); *A61K 47/10* (2013.01); *A61K 47/14* (2013.01); *A61K 47/20* (2013.01); *A61K 47/22* (2013.01); *A61K 47/26* (2013.01); *A61K 2300/00* (2013.01)

(58) Field of Classification Search
CPC .......... A61P 19/02; A61P 19/08; A61L 27/52; A61L 27/54; A61L 2400/06; A61K 9/7007; A61K 9/0019; A61K 47/6903; A61K 47/10
See application file for complete search history.

(56) References Cited

U.S. PATENT DOCUMENTS

| | | | |
|---|---|---|---|
| 5,603,959 A | 2/1997 | Horrobin | |
| 6,031,017 A * | 2/2000 | Waki | A61L 15/28 522/84 |
| 6,471,970 B1 | 10/2002 | Fanara | |
| 7,749,485 B2 | 7/2010 | Tournier | |
| 10,300,023 B1 | 5/2019 | Karp | |
| 2005/0084470 A1 | 4/2005 | Abbas | |
| 2005/0267036 A1* | 12/2005 | Garry | C07K 5/1021 514/18.3 |
| 2005/0287198 A1* | 12/2005 | Murthy | A61K 9/0014 424/450 |
| 2006/0276676 A1 | 12/2006 | Van Bommel | |
| 2008/0004398 A1 | 1/2008 | Durrieu | |
| 2008/0038316 A1 | 2/2008 | Wong | |
| 2009/0048296 A1 | 2/2009 | Campbell | |
| 2009/0110735 A1 | 4/2009 | Maggio | |

(Continued)

FOREIGN PATENT DOCUMENTS

| | | |
|---|---|---|
| EP | 0517211 | 6/1992 |
| EP | 1063007 | 12/2000 |

(Continued)

OTHER PUBLICATIONS

ThoughCo. Phosphate-Buffered Saline or PBS Solution. Jun. 4, 2018. <https://www.thoughtco.com/phosphate-buffered-saline-pbs-solution-4061933>. (Year: 2018).*
Bennett, et al., "Next-generation hydrogel films as tissue sealants and adhesion barriers," Cardiac Surgery 18:494-9 (2003).
Bhattacharya, et al., "In Molecular Gels," Kluwer Academic Publishers: The Netherlands (2004).
Bhuniya, et al., "(S)-(+)-Ibuprofen-Based Hydrogelators: An Approach Toward Anti-Inflammatory Drug Delivery," Tetrahedron Lett., 47:7153-6 (2006).
Bong, et al., Angew. "Self-Assembling Organic Nanotubes," Chem. Int. 40:988-1011 (2001).

(Continued)

*Primary Examiner* — Tracy Liu
(74) *Attorney, Agent, or Firm* — Pabst Patent Group LLP

(57) ABSTRACT

A gel formulation has been developed which provides high loading, e.g., between about 5% and about 50% wt/wt agent/total gel weight, of a wide range of agents, especially amine-containing compounds such as local anesthetic agents that are known to be difficult to encapsulate, and which adhere to charged surfaces. Examples of pharmaceutically important amines include anesthetics, such as lidocaine. Tuning the ionic strength of an aqueous medium during preparation, suspension, and dialysis purification of the hydrogel composition allows for retention and/or control of agent loading contents, as well as a high capacity for adhesion to charged surfaces mimicking inflamed tissue. In some instances, the rheological properties of the gel can be tuned such as to impart thixotropic properties to the gels formed.

29 Claims, 4 Drawing Sheets

(56) References Cited

U.S. PATENT DOCUMENTS

| | | | |
|---|---|---|---|
| 2009/0169498 A1 | 7/2009 | De Jong | |
| 2009/0263489 A1* | 10/2009 | Zanella | A61K 9/0024 424/490 |
| 2010/0129451 A1 | 5/2010 | John | |
| 2011/0229565 A1 | 9/2011 | Karp | |
| 2012/0022158 A1* | 1/2012 | Niu | A61K 9/0014 514/537 |
| 2012/0189588 A1* | 7/2012 | Nahas | A61K 31/00 424/93.7 |
| 2013/0273140 A1 | 10/2013 | Maggio | |
| 2013/0280334 A1* | 10/2013 | Karp | A61K 9/0019 424/490 |
| 2013/0309286 A1 | 11/2013 | Engstad | |
| 2014/0302144 A1 | 10/2014 | Koutsopoulos | |
| 2015/0018387 A1* | 1/2015 | Campbell | A61K 9/0014 514/312 |
| 2015/0202586 A1 | 7/2015 | Imoto | |
| 2015/0297731 A1* | 10/2015 | Chiou | A61K 9/0051 514/236.2 |
| 2016/0243026 A1* | 8/2016 | Pathak | A61K 9/0021 |
| 2017/0319500 A1 | 11/2017 | Karp | |
| 2018/0050055 A1* | 2/2018 | Ahmed | A61K 31/7012 |

FOREIGN PATENT DOCUMENTS

| | | |
|---|---|---|
| EP | 2361640 | 2/2010 |
| FR | 2417494 | 9/1979 |
| WO | 9907416 | 2/1999 |
| WO | WO 99/07416 | 2/1999 |
| WO | 2003006043 | 1/2003 |
| WO | 2005056039 | 6/2005 |
| WO | 2006008386 | 1/2006 |
| WO | WO 2006/008386 | 1/2006 |
| WO | 2010033726 | 3/2010 |
| WO | WO 2010/033726 | 3/2010 |
| WO | 2012040623 | 3/2012 |
| WO | WO 2012/040623 | 3/2012 |
| WO | 2014041378 | 3/2014 |
| WO | 2014089472 | 6/2014 |
| WO | WO 2014/089472 | 6/2014 |

OTHER PUBLICATIONS

Bonte and Juliano, "Interactions of liposomes with serum proteins", Chem Phys Lipids, 40:359-72 (1986).
Boutaud, et al., J.A. "Determinants of the Cellular Specificity of Acetaminophen as an Inhibitor of Prostaglandin H(2) Synthases," PNAS, 99:7130-5 (2002).
Browne, et al., "Clinical outcome of autologous chondrocyte implantation at 5 years in US subjects", Clin Orthop Relat Res., 436:237-45 (2005).
Bryers, et al., "Biodegradtion of Poly(anhydride-esters) into Non-Steroidal Anti-Inflammatory Drugs and Their Effect on Pseudomonas aeruginosa Biofilms In Vitro and on the Foreign-Body Response In Vivo," Biomaterials, 27:5039-48 (2006).
Burns, et al., "Physical characterization and lipase susceptibility of short chain lecithin/triglycer mixed micelles potential lipoprotein models", J Biol Chem., 256(6):2716-22 (1981).
Casuso, et al., "Converting drugs into gelators: supramolecular hydrogels from N-acetyl-L-cysteine and coinage-metal salts", Org Biomol Chem., 8:5455-8 (2010).
Choi, et al., "Studies on gelatin-based sponges. Part III: A comparative study of cross-linked gelatin/alginate, gelatin/hyaluronate and chitosan/hyaluronate sponges and their application as a wound dressing in full-thickness skin defect of rat", J Materials Sci., 12:67-73 (2001).
Chourasia, et al., "Pharmaceutical Approaches to Colon-Targeted Drug Delivery Systems," Pharm. Pharmaceut. Sci., 6:22-66 (2003).
Donati, et al., "Synergistic effects in semidilute mixed solutions of alginate and lactose-midified chitosan (chitlac)", Biomacromolecules, 8:957-62 (2007).

Erdmann, et al., "Degradable Poly(anhydridie ester) Implants: Effects of Localized Salicylic Acid Release on Bone," Biomaterials, 21:2507-12 (2000).
Estroff, et al., "Effective Gelation of Water Using a Series of Bis-urea Dicarboxylic Acids," Angew. Chem. Int. Ed. 39:3447-50 (2000).
Fischel-Ghodsian, et al., "Enzymatically Controlled Drug Delivery," PNAS, 85:2403-6 (1988).
Friggeri, et al., "Entrapment and release of quinoline derivatives using a hydrogel of a low molecular weight gelator", Controlled Release, 97:241-8 (2004).
Gong, et al., "Synthesis ofhydrogels with extremely low surface friction", J. Am. Chem. Soc., 123:5582 (2001).
Gopinath, et al., "Ascorbyl palmitate vesicles (aspasomes): formation characterization and applications", Intl J Pharma., 271(1-2):95-113 (2004).
Gupta, et al., "Hydrogels.from controlled release to pH-responsive drug delivery", Drug Discovery Today, 7:569-79 (2002).
Han, et al., "Catalytic ester-amide exchange using group (iv) metal alkoxide-activator complexes", JACS, 127:10039-44 (2005).
Hans, et al., "Synthesis and characterization ofmPEG-PLA prodrug micelles", Biomacromolecules, 6, 2708-17 (2005).
Harten, et al., "Salicylic acid-derived poly(anhydride-esters) inhibit bone resorption and formation in vivo", Biomed. Mater. Res-A 72A:354-62 (2005).
Hoare, et al., "Hydrogelsin drug delivery: Progress and challenges", Polymer, 49:1993-2007 (2008)/.
Hunziker, "Articular cartilage repair: basic science and clinical progress. A review of the current status and prospects", Osteoarthritis Cartilage, 10:432-63 (2002).
INDOMETHACIN_MSDS_Jun. 19, 2012.
Jen, et al., "Review. Hydrogels for cell immobilization", Biotechnol, Bioeng.,50: 357-64 (1996).
John, et al., "Enzymatically Derived Sugar-Containing Self-Assembled Organogels with Nanostructured Morphologies,"Agnew. Chem. Int. Ed., 45:4772-5 (2006).
John, et al., "Lipid-based nanotubes as functional architectures with embedded fluorescence and recognition capabilities", J. Am. Chem. Soc., 126:15012-3 (2004).
John, et al., "Morphological control of helical solid bilayers in high-axial-ratio nanostructures through binary self-assembly", Chem. Eur. J., 8:5494-500 (2002).
John, et al., "Nanotube Formation from Renewable Resources via Coiled Nanofibers", AdV. Mater.,13:715-8 (2001).
John. et al., "Unsaturation effect on gelation behavior ofaryl glycolipids", Langmuir, 20:2060-5 (2004).
Jovanovic, et al., "How curcumin works preferentially with water soluble antioxidants", Chem. Soc., 123, 3064-68 (2001).
Jung, et al., "Self-Assembly ofa Sugar-Based Gelator in Water. Its Remarkable Divers ity in Gelation Ability and Aggregate Structure, " Langmuir 17, 7229-32 (2001).
Kalgutkar, et al, "Ester and Amide Derivatives of the Nonsteriodal Antiinflammatory Drug,Indomethacin, as selective cyclooxygenase-2 inhibitors," J. Med. Chem.,43:2860-70 (2000).
Kamath, et al., "Biodegradable Hydrogels in Drug Delivery," Adv. Drug Deliv. Rev., 11:59-84 (1993).
Kim, et al., "In vivo evaluation of polymeric micellar paclitaxel formulation. toxicity and efficacy", Controlled Release, 72:191-202 (2001).
Kitagawa, et al., "Cationic Vesicles Consisting of 1,2-Dioleoyl-3-Trimethylammonium Propane (DOTAP) and Phosphatidylcholines and Their Interaction with Erythrocyte Membrane", Chem Pharma Bull., 52(4):451-3 (2004).
Kiyonakam, et al., Semi-wet peptide/protein array using supramolecular hydroge , Nat. Mater., 3:58-64 (2004).
Kohane, et al., "A re-examination of tetrodotoxin for prolonged duration local anesthesia", Anesthesiology, 89(1):119-131 (1998).
Kumar, et al. "Prodrugs as self-assembled hydrogels: a new paradigm for biomaterials", Biotech., 24:1-9 (2013).
Kumar, et al., "First snapshot of a nonpolymeric hydrogelator interacting with its getting solvents", Chem. Commun., 4059-62 (2005).

(56) References Cited

OTHER PUBLICATIONS

Lee, et al., "Hydrogels for Tissue Engineering," Chem. Rev., 101:1869-80 (2001).
Li, et al., "Molecular nanofibers of olsalazine form supramolecular hydrogeis for reductive release of an anti-inflammatory agent", JACS, 132:17707-9 (2010).
Loos, et al., "Design and Application of Self-Assembled Low Molecular Weight Hydrogels," Eur. J.of Organic Chem., 17:3615-31 (2005).
Lu, et al., "Photopolymerization of multilaminated poly(HEMA) hydrogels for controlled release", J Controlled Release, 57:291-300 (1999).
Luboradzki, et al., "An Attempt to Predict the Gelation Ability of Hydrogen-Bond-Based Gelators Utilizing a Glycosidase Library," Tetrahedron 56:9595-9 (2000).
Magnussen, et al., "Treatment of focal articular cartilage defects in the knee: a systematic review", Clin Orthop Relat Res, 466:952-96 (2008).
Makarevic, et al., "Bis(amino acid) oxalyl amides as ambidextrous aelators of water and organicsolvents. supramolecular gels with temperature dependent assembly/dissolution equilibrium", Chem. Eur. J. 7:3328-41 (2001).
Marsich, et al., "Alginate/lactose-modified chitosan hydrogels: A bioactive biomaterial for chondrocyte encapsulation", J Biomat Mater Res A, 84(2):364-76 (2008).
Mazumdar, et al., "Preparation and evalulation ofethambutol derivatives." Indian J. Pharm. Sci., 47: 179-80 (1985).
Menger, et al., "Anatomy ofa Gel. Amino Acid Derivatives that Rigidify Water at Submillimolar Concentrations," J. Am. Chem. Soc. 122:11679-91 (2000).
Miyata, et al., "Biomolecule-Sensitive ydrogels," Adv. Drug Deily. Rev., 54:79-98 (2002).
Moliner, et al., "PFGSE-NMR study of the self-diffusion of sucrose fatty acid monoesters in water", J Colloid Interface Sci., 286(1):360-8 (2005).
Nicolaou, et al., "A Water-Soluble Prodrug of Taxol with Self-Assembling Properties," Agew.Chem. Int. Ed., 33: 1583-7 (1994).
Nishimura, et al., "Analysis of reducing end-groups produced by enzymatic scission of glycoside linkages in O-methylcellulose", Carbohydrate Res., 267:291-8 (1995).
Oda, et al., "Gemini Surfactants as New, Low Molecular Weight Gelators of Organic Solvents and Water," Angew. Chem. Int. Ed., 37, 2689-91 (1998).
Palma, et al., "Evaluation of the surfactant properties of ascorbyl palmitate sodium salt", Eu J Pharma Sci., 16(1-2):37-43 (2002).
Peppas, et al., "Hydrogels in Biology and Medicine. From Molecular Principles to Bionanotechnology", Adv. Mater., 18:1345-1360 (2006).
Peppas, et al., "Hydrogels in pharmaceutical formulations," Eur. J. Pharm. Biopharm., 50:27-46 (2000).
Peppas, "Hydrogels and Drug Delivery," Curr. Opin. Colloid Interface Sci., 2:531-7 (1997).
Persico, et al., "Effect of tolmetin glycine amide (McN-4366) a prodrug of tolmetin sodium on adjuvant arthritis in the rat", J Pharma Exp Therap., 247(3):889-96 (1988).
Vemula, et al., "Smart Amphiphiles. Hydro/Organogelators for in Situ Reduction of Gold", Chem.Commun., 2218-2220 (2006b).
Vemula, et al., "Encymc Catalysis. Tool to Make and Break Amygdalin Hydrogelators from Renewable Resources. A Delivery Model for Hydrophobic Drugs"; J. Am. Chem, Soc., 128: 8932-8 (2006).
Vemula, et al., "In Situ Synthesis of Gold Nanoparticles using Molecular Gels and Liquid Crystals from Vitamin-C Amphiphiles," Chem. Mater., 19:138-40 (2007).
Vigroux, et al.; "Cyclization-activated prodrugs: N-(substituted 2-hydroxyphenyl and 2-hydroxypropyl)carbamates based on ring-opened derivatives of active benzoxazolones and oxazolidinones as mutual prodrugs of acetaminophen", J Med Chem., 38:3983-94 (1995).

Vohra, et al., "Nanolipi carrier-based thermoreversible gel for localized delivery of docetaxel to breast cancer", Cancer Nanotechnol., 4(1-3):1-12 (2013).
Wang, et al., "Low Molecular Weight Organogelators for Water," Chem. Commun. 310-11 (2003).
Wang, et al., "Hydrogels as separation agents, Responsive Gels. Volume Transitions II," Advances in Polymer Science, 67-79 (1993). Abstract Only.
Whitesides, et al., "Beyond molecules. self-assembly of mesoscopic and macroscopic components ", PNAS, 99:4769-74 (2002).
Xing, et al., "Hydrophobic Interaction and Hydrogen Bonding Cooperatively Confer a Vancomycin Hydrogel. A Potential Candidatefor Biomaterials," J. Am. Chem. Soc. 124:14846-7 (2002).
Yan, et al., "Enzymatic Production of sugar Fatty Acids Esters," PhD thesis, University of Stuttgard, (2001).
Yang, et al., "A simple visual assay based on small molecule hydrogels for detecting inhibitors of enzymes," Chem. Commun., 2424-25 (2004c).
Yang, et al., "Enzymatic Formation of Supramolecular Hydrogels," Adv. Mater., 16:1440-4 (2004b).
Yang, et al., "Enzymatic Hydrogelation of small Molecules", Ace. Chem. Res.; 41:315-26 (2008).
Yang, et al., "Small Molecular Hydrogels Based on a Class of Anti-Inflammatory Agents," Chem. Commun., 208-9 (2004).
Yang, et al., "Using a Kinase/Phosphatase Switch to Regulate a Supramolecular Hydrogel and Forming the Supramolecular Hydrogel In Vivo," J. Am. Chem. Soc. 128:3038-43 (2006).
Zhang and Weiss, "Self-assembled networks and molecular gels derived from long-chain, naturally-occurring fatty acids", J Brazilian Chem Soc., 27(2):239-55 (2015).
Zhang, et al., "An inflammation-targeting hydrogel for local drug delivery in inflammatory bowel disease", Sci Transl Med., 7(300):300ra128 (2015).
Zhang, et al., "Hydrogels: Wet or Let Die," Nature Materials 3:7-8 (2004).
Zhang, et al., "Versatile small-molecule motifs for self-assembly in water and the formation of biofunctional supramolecular hydrogels", Langmuir; 27(2):529-37 (2011).
International Search Report for PCTIUS2009/057349 dated May 6, 2009.
International Search Report and Written Opinion for PCT/US2011/053075 dated Apr. 17, 2012.
Pietzyk, et al., "Degradation of phosphatidylcholine in liposomes containing carboplatin in dependence on composition and storage conditions", Intl J Pharma., 196(2):215-8 (2008).
Poulsen, et al., "Effect of topical vehicle composition on the in vitro release of fluocinolone acetonide and its acetate ester", J Pharma Sci., 57(6):928-33 (1968).
Qiu, et al., "Environment-sensitive hydrogels for drug delivory,"Adv. Drug Deliv. Rev., 53, 321-39 (2001).
Rajabalaya, et al., "Studies on effect of plasticizer on invitro release and exvivo permeation from eudragit e100 based chlorpheniramine maleate matrix type transdermal delivery system", J Excipients Food Chem., 1(2):1-12 (2010).
Rattie, et al., "Acetaminophen Prodrugs III, Hydrolysis of Carbonate and Carboxylic Acid Esters in Aqueous Buffers," J. Pharm. Sci., 59:1738-41 (1970).
Robinson, et al., "Design, synthesis, and biological evaluation of angiogenesis inhibitors Aromatic enone and dienone analogues of curcumin", Bioru. Med. Chem. Lett., 13:115-17 (2003).
Rooseboom, et ale "Enzyme-catalyzed activation of anticancer prodrugs", Pharmacol. Rev., 56:53-102 (2004).
Scogs, substances list, http://www.fda.gov/Food/IngredientsPackagingLabeling/GRAS/SCOGS/ucm084104. Retrieved from interner Apr. 3, 2014.
Sinha, et al., "Microbially triggered drug delivery to the colon", Eur. J. Pharm. Sci, 18:3-18 (2003).
Sreenivasachary, et al., "Gelation-driven component selection in the generation of constitutional dynamic hydrogels based on guanine-quartet formation", PNAS, 102:5938-43 (2005).
Szuts, et al., "Study of thermos-sensitive gel-forming properties of sucrose stearates", J Excipients Food Chem., 1(2):13-20 (2010).

(56) References Cited

OTHER PUBLICATIONS

Tomsic, et al., "Internally self-assembled thermoreversible gelling mulsions:ISAsomes in methylcellulose, k-carragrrnan, and mixed hydrogels", Langmuir, 25:9525 (2009).
Toth and Urtis, "Commonly used muscle relaxant therapies for acute low back pain: A review of carisoprodol cyclobenzaprine hydrochloride, and metaxalone", Clin Therap., 26(9):1355-67 (2004).
Trouet, et al., "Extracellularly tumor-activated prodrugs for the selective chemotherapy of cancer application to doxorubicin and preliminary in vitro and in vivo studies", Cancer Res., 61: 2843-6 (2001).
Troung, et al., "Self assembled gels for biomedical applications", Focus Rev., 6:30-42 (2011).
Ullrich, et al., "Sucrose ester nanodispersions: Microviscosity and viscoelastic properties", Eu J Pharma Biopharma., 70:550-5 (2008).
Van Bornmel et al., "Two-stage enzyme mediated drug release from LMWG gydrogels," Org.Biomol. Chem. 3:2917-2920 (2005).
Van der Linden, et al., "Clinic/us-scnsi/ivc hydrogels and their applications in chemical a nonpolymeric hydrogelator interacting with its gelling solvents", Chem. Commun., 4059-62 (2005).
Van der Linden, et al., "Stimulus-sensitive hydrogels and their applications in chemical (micro)analysis", Analyst, 128:325-31 (2003).
Van Esch, et al., "New functional materials based om self-assembling organogels: from serendipity towards design", Angew Chem Int., 39:2263-66 (2000).
Vassilev, et al., "Enzymatic Synthesis of a Chiral Gelator with Remarkably Low Molecular Weight,"Chem. Commun., 1865-6 (1998).
International Search Report for PCT/US2016/056070 dated Jan. 12, 2017.
Preliminary Report on Patentability for PCT/US2011/053075 dated Mar. 26, 2013.
European Search Report for EP 11827647 dated Jul. 16, 2014.
International Search Report for PCT/US2016/031614 dated Jul. 26, 2017.
International Search Report for PCT/US2017/031615 dated Sep. 25, 2017.
International Preliminary Report on Patentability issued in PCT/US2009/057349 dated Mar. 22, 2011.
Preliminary Report on Patentability for PCT/US2016/056070 dated Jan. 12, 2017.
Burns, et al., "Physical characterization and lipase susceptibility of short chain lecithin/triglycer mixed micelles potential lipoprotein models", J Biol Chem., 256(6):2716-22.
Jen, et al., "Review. Hydrogels for cell immobilization", *Biotechnol. Bioeng.*,50: 357-64.
Jung, et al., "Self-Assembly ofa Sugar-Based Gelator in Water. Its Remarkable Divers ity in Gelation Abilitv and Aggregate Structure, " *Lanumuir* 17, 7229-32 (2001).

Kalgutkar, et al., "Ester and Amide Derivatives of the Nonsteriodal Antiinflammatory Drug,Indomethacin, as selective cvclooxvgenase-2 inhibitors," *J. Med. Chem.*,43:2860-70 (2000).
Kiyonakam, et al., Semi-wet peptide/protein array using supramolecular hydrogel, *Nat. Mater.*, 3:58-64 (2004).
Makarevic, et al., "Bis(amino acid) oxalyl amides as ambidextrous gelators of water and organicsolvents. supramolecular gels with temperature dependent assembly/dissolution equilibrium", *Chem. Eur. J.* 7:3328-41 (2001).
Miyata, et al., "Biomolecule-Sensitive ydrogels," *Adv. Drug Deliv. Rev.*, 54:79-98 (2002).
Rooseboom, et al., "Enzyme-catalyzed activation of anticancer prodrugs", *Pharmacol. Rev.*, 56:53-102 (2004).
Troung, et al., "Self assembled gels for biomedical applications", *Focus Rev.*, 6:30-42.
Van Bommel et al., "Two-stage enzyme mediated drug release from LMWG gydrogels," Org.Biomol. Chem. 3:2917-2920 (2005).
Yang, et al., "Small Molecular Hydrogels Based on a Class of Anti-Inflammatory Agents," *Chem. Commun.*, 208-9 (2004c).
International Search Report for PCT/US2009/057349 dated May 6, 2009.
Vallecillo, et al., "A liquid crystal of ascorbyl palmitate, used as vaccine platform, provides sustained release of antigen and has intrinsic pro-inflammatory and aduvant actvities which are dependent on MyD88 adaptr protein", Journal of Controlled Release 214:12-22 (2015).
International Search Report PCTUS2019/025782 dated Jun. 26, 2019.
International Search Report for PCT application PCT/US2018/016835 mailed Jul. 12, 2018.
Karim, et al., "Effectiveness and Safety of Tenofovir Gel, and Antiretroviral Microbicide, for the Prevention of HIV Infection in Women", Science, 329:1168-1174 (2010).
Krog and Sparse, "Food emulsifiers: their chemical and physical properties", Food Emulsions,Fourth Ed., pp. 45FF, CRC Press (2004).
Li, et al., Thermosensitive hydrogel of hydrophobically-modified methylcellulose for intravaginal drug delivery, J. Mater. Sci.: Mater. Med., 23:1913-1919 (2012).
Mahalingam, et al., "Design of a Semisolid Vaginal Microbicide Gel by Relating Composition to Properties and Performance", Pharm. Res., 27:2478-2491 (2010).
Vinson, et al., "Direct imaging of surfactant micelles, vesicles, discs, and ripple phase structures by cryo-transmission electron microscopy", Journal of Colloid Ans Interface Science, 142(1):74-91 (1991).
Zidan, et al., "Maximized Mucoadhesion and Skin Permeation of Anti-AIDS-Loaded Niosomal Gels", Pharmaceutics, Drug Delivery and Pharmaceutical Technology, 103:952-964 (2014).

* cited by examiner

FORMULATION OF NANOSTRUCTURED GELS FOR INCREASED AGENT LOADING AND ADHESION

CROSS-REFERENCE TO RELATED APPLICATIONS

This application claims benefit of and priority to U.S. Provisional Application No. 62/502,872, filed on May 8, 2017, which is hereby incorporated herein by reference in its entirety.

FIELD OF THE INVENTION

This is generally in the field of drug delivery formulations employing low molecular weight, self-assembled nanostructures.

BACKGROUND OF THE INVENTION

One of the proposed means for providing a high local drug concentration while minimizing systemic toxicity is to formulate drug in a depot, such as a gel which provides controlled or sustained release of the drug. However, it is difficult to encapsulate high levels of drug in a gel without most being released in a burst immediately after administration in vivo. Factors such as the hydrophilicity/hydrophobicity of an agent and its non-covalent interactions with the gel matrix strongly influence encapsulation efficiency and loading dosage. Co-solvent systems have been utilized including both aqueous and organic solvents (e.g., water and dimethyl sulfoxide, or water and alcohol) to prepare drug-loaded gel matrices, especially those formed from assembly between gelators and drug agents. See, for example, (U.S. Patent Application Publication Nos. 20130280334 and 20110229565. However, hydrophilic molecules may not be effectively encapsulated in these co-solvent systems. Molecules containing charges, e.g., tertiary amine in local anesthetics, impact the pH and charge-charge interactions in the gel matrix formulation. Additionally, hydrogel or organogel drug depots often have limited affinity for the inflamed tissue sites unless modified with the addition of targeting or adhesion ligands.

A number of drugs have systemic side effects. For example, local anesthetics may cause myotoxicity and neurotoxicity (Padera, et al., *Anesthesiology*, 108(5):921-928 (2008); Pere, et al., *Reg Anesth*, 18(5):304-307 (1993); Zimmer, et al., *Anaesthesist*, 56(5):449-453 (2007); Yamashita, et al., *Anesth Analg*, 97(2):512-519 (2003)). It is extremely difficult to encapsulate effective amounts of potent local anesthetics in hydrophilic gel matrices since the agents are hydrophilic, and since initial rapid release or leaching can lead to systemic toxicity (Barnet, et al., *Anesth Analg*, 101(6):1838-1843 (2005); Kohane, et al., *Anesthesiology*, 89(1):119-131 (1998)).

Therefore, it is an object of the present invention to provide self-assembled hydrogel formulations with high loading of difficult-to-encapsulate agents and minimal leaching during formulation and post-formulation processes such as suspension and purification of the gel.

It is another object of the present invention to provide self-assembled hydrogel formulations wherein the gels have tunable rheological properties.

It is yet another object of the present invention to provide a formulation and a method of delivering large amounts of agents to sites of inflammation with increased dosing efficacy and adhesion specificity.

SUMMARY OF THE INVENTION

A gel formulation has been developed which provides high loading, e.g., between about 5% and about 30% wt/wt agent/total gel weight, of a wide range of amine-containing compounds such as local anesthetic agents that are known to be difficult to encapsulate in hydrogel formulations, and which adhere to charged surfaces. Amine-containing compounds may have primary, secondary, tertiary, and/or quaternary amines. Examples of pharmaceutically important amines include anesthetics and anti-infectives. In preferred embodiments, the agent is a local anesthetic such as lidocaine, procaine, tetracaine, dibucaine, benzocaine, bupivacaine, or salt thereof such as lidocaine hydrochloride, procaine hydrochloride, tetracaine hydrochloride, dibucaine hydrochloride, benzocaine hydrochloride, or bupivacaine hydrochloride.

The gel is formed from the self-assembly and/or non-covalent interactions of a generally recognized as safe (GRAS) amphiphilic gelator and one or more therapeutic, prophylactic, or diagnostic agents encapsulated in the gel. In some forms, the gelator has a molecular weight of 2,500 or less, and is an ascorbyl alkanoate, a sorbitan alkanoate, a triglycerol monoalkanoate, or a sucrose alkanoate. Self-assembled gel is formed in a liquid medium such as distilled water, de-ionized water, pure or ultrapure water, saline, or other physiologically acceptable aqueous solutions containing salts (e.g., at, between or greater than 0 and 0.15 M NaCl; or between 10 mM and 500 mM), or a two-solvent system including an organic solvent and water (or an aqueous salt solution). Exemplary organic solvents are dimethyl sulfoxide (DMSO), methanol, acetone, ethanol, dioxane, acetonitrile, toluene, tetrahydrofuran, isobutyl alcohol, polyethylene glycol at a low molecular weight (e.g., 1 kDa) which is liquid at 37° C., propylene glycol, and dipropylene glycol.

Generally an organic solvent is mixed with and at least partially dissolves one or more gelators. Depending on the hydrophobicity or hydrophilicity, the amine-containing compounds may be dissolved in the co-solvent mixture or the aqueous solution which is then added to the gelator in the organic solvent. In a first embodiment, the agent is added to gelator dissolved in a co-solvent medium including both water (or an aqueous buffer or salt solution) and a water-miscible organic solvent with mixing and optionally heating to insure complete dissolution. In a second embodiment demonstrated in the examples, the gelators are dissolved initially in an organic solvent to form a solution with the gelators as the solutes (termed "gelator solution"). The agent, for example, free base lidocaine, is then dissolved in the gelator solution. An aqueous solution such as pure water or an aqueous buffer or salt solution is then mixed with the drug-gelator solution to form a liquid gel solution. The amount of the organic solvent in the total amount of liquid (organic+water/aqueous solution) is generally no more than 50%. If needed, the liquid gel solution is heated to insure complete dissolution, then cooled to form a gel stable to inversion at room temperature (25° C.) or body temperature (37° C.). Agent is added to form a final concentration in the gel of between about 4 and 25 wt/%. The amount of the organic solvent is generally between about 5% to about 50% by volume in the combined amount of the organic solvent and water (or an aqueous solution). Even if a higher % amount of the organic solvent is present in the gelator solution, most of the organic solvent in a self-assembled gel can be removed and replaced with media in purification techniques such as dialysis, centrifugation, and filtration.

Salt or buffer aqueous solutions may increase agent (i.e., drug) loading. For example, dissolving amphiphilic gelators in DMSO, then adding phosphate buffered saline (PBS) at a physiological ionic strength increases loading of amine-containing compounds in the resulting self-assembled gel, compared to water. As demonstrated in the example, inclusion of PBS increased loading of the amine-containing agent such as lidocaine or lidocaine hydrochloride to at least 4%, 6%, 8%, 10%, 15%, or 18% by weight, or greater in a gel formed in a DMSO-PBS system, whereas ultrapure water or water with essentially no salt formed a gel in a DMSO-water system encapsulating less than 0.5%, 1%, 2%, or 3% by weight of lidocaine or salts thereof.

In some instances, the inclusion of salt(s) during formation of gel, such as by adding salt(s) to buffer aqueous solutions, can be used to tune the rheological properties of the gel, such as to impart thixotropy. For example, dissolving amphiphilic gelators in an organic solvent, such as DMSO, and adding phosphate buffered saline (PBS) containing one or more salts imparts thixotropic properties to the self-assembled gel, as compared to using water or a buffer solution without additional salt(s). Exemplary salts which can be added to tune the rheological properties of the gels include, but are not limited to sodium chloride, potassium chloride, calcium chloride, magnesium chloride, zinc chloride, or combinations thereof. Any suitable salt can be used that can provide sodium, potassium, calcium, magnesium, or zinc ions. In some instances, the salt(s) are added during gel formation. In some other instances, the salt(s) are added post-gel formation, such as during a post-processing step.

In some instances, the inclusion of organic solvent(s) during formation of gel or added post-gel formation, such as during a post-processing step to tune the rheological properties of the gel, such as to impart thixotropy. Exemplary organic solvents which can be used, either alone or in combination with the salt(s) already discussed, to tune the rheological properties of the gels include, but are not limited to dimethylsulfoxide (DMSO), alcohols (such as methanol, ethanol, isopropanol, t-butanol). In some other instances, the organic solvent(s) described here are added as part of gel formation or can be added to buffer(s), such as a phosphate buffer, in which a prepared gel may be resuspended to provide gels having organic solvent(s) present therein.

In some instances, a combination of both salt(s) and organic solvent(s) can be used to tune the rheological properties of the gel, such as to impart thixotropy. The inclusion of salt(s) and/or solvent(s) demonstrates that the rheological properties can be controlled or tuned without altering the concentration of gelator (such as ascorbyl palmitate) or agent (such as lidocaine) in the gel formulation. Control over rheological properties is an important invention because the viscosity and rheology of a locally administered therapeutic can affect its disposition to the tissue in question.

In some instances, the gels can be formed without any additional salts and/or organic solvents or their rheological properties can be tuned by addition of salts and/or organic solvent(s) (either during gel formation or post-gel formation). The gels described can have or can be tuned to have a storage modulus (G') of from about 0.1, from about 0.2, from about 0.3, from about 0.4, from about 0.5, from about 0.6, from about 0.7, from about 0.8, from about 0.9, from about 1, from about 2, from about 3, from about 4, or from about 5 Pascals up to about 50, about 75, about 100, about 150, about 200, about 250, or about 300, or any combination of upper and lower end points disclosed herein.

In some instances, the gels can be formed without any additional salts and/or organic solvents or their rheological properties can be tuned by addition of salts and/or organic solvent(s) (either during gel formation or post-gel formation). The gels described can have or can be tuned to have a loss modulus (G") of from about 0.1, from about 0.2, from about 0.3, from about 0.4, from about 0.5, from about 0.6, from about 0.7, from about 0.8, from about 0.9, from about 1, from about 2, from about 3, from about 4, or from about 5 Pascals up to about 10, about 15, about 20, about 25, about 30, about 35, about 40, or about 300 Pascals, or any combination of upper and lower end points disclosed herein.

In some instances, the gels formed with or without addition of salts and/or organic solvent(s) (either during gel formation or post-gel formation) have can have viscosities in a range from between about 0.1, from about 0.2, from about 0.3, from about 0.4, from about 0.5, from about 0.6, from about 0.7, from about 0.8, from about 0.9, from about 1, from about 2, from about 3, from about 4, or from about 5 centipoise (cP) up to about 10, about 100, about 200, about 300, about 400, about 500, about 600, about 700, about 800, about 900, about 1,000, about 1,100, about 1,200, about 1,300, about 1,400, about 1,500, about 1,600, about 1,700, about 1,800, about 1,900, about 2,000, about 2,500, or about 3000 cP, or any combination of upper and lower end points disclosed herein. In some instances, the gels formed addition of salts and/or organic solvent(s) (either during gel formation or post-gel formation) exhibit thixotropic properties such that the viscosity of the gel changes upon exposure to shear, for example.

In some embodiments where gels are formed in a two-solvent system (e.g., in a DMSO-PBS system), increasing the proportion of the organic solvent relative to the aqueous salt solution results in an increase in the loading and encapsulation efficiency of amine-containing agents. Increasing the volume ratio of an organic solvent (e.g., DMSO) to an aqueous salt solution (e.g., phosphate-buffered saline) from 1:4 to 1:1 resulted in an increase of agent loading such as lidocaine loading in the self-assembled gel.

In other embodiments where amphiphilic gelators are first dissolved in an organic solvent such as methanol, increasing the amount of salt in an aqueous phase to add to the methanol solution for gelation upon heating and cooling results in a decrease in the agent loading and encapsulation percentages.

The gel formulation can be further processed to remove solvent, solvent impurities, excess agent (i.e., drug or free drug), for example, using dialysis, centrifugation, and/or filtration (e.g., tangential flow filtration (TFF)). In a preferred embodiment, solvent residue is removed to less than 1%, 3%, 5%, or 10% of the starting levels, or to less than the acceptance criteria of residual solvents by U.S. Pharmacopeia Convention, International Conference on Harmonization guidance, or by U.S. Food and Drug Administration). In some forms, dialysis or TFF in an aqueous medium with zero to less than 0.15 M salt effectively retains a greater amount of agent (i.e, drug) and maintains the high agent loading in a hydrogel as compared to dialysis in an aqueous medium with 0.15 M or a greater amount of salt.

Following formation of a self-supporting gel that is consistent, homogeneous, and stable to inversion, the gel may be suspended or purified in a pharmaceutically acceptable carrier to generate a desired volume for administration. Water or an aqueous medium with a low concentration of salt (e.g., less than 0.15 M) as the medium for suspension of the drug-loaded gel maintains the high loading content of the agent to at least 80%, 85%, 90%, 95%, or about 100% compared to the hydrogel composition before suspension; whereas phosphate buffered saline or aqueous medium containing about 0.15 M salt maintains about 65%, 70%, 75%, or 80% of the encapsulated agent content compared to before suspension. Suspension of a gel composition can provide a desired final volume of the formulation for ease of administration (e.g., for ease of administration to a patient in need thereof by drinking or injection) and/or a desired agent concentration to control toxicity. The gel can also be dried or lyophilized to remove all solvent, administered in dried form, or rehydrated for administration. Although the self-assembled gel is stable to inversion, i.e., it does not flow when inverted at ambient temperature (e.g., below the Krafft point of gelator) and pressure, the suspended gel in a pharmaceutically acceptable carrier may flow due to gravity.

In some embodiments the gel is suspended in a pharmaceutically acceptable carrier and then the gel dispersed or broken to form fibers or particles. Dispersion techniques include agitation, vortexing, pipetting, and homogenizing.

The gel formulation with a high loading content of amine-containing compounds (e.g., a self-supporting gel, a fibrous gel in the suspension medium, and a purified gel) adheres to a charged surface, such as those with amine functional groups on the surface. A lower or no ionic strength suspension medium (e.g., zero to less than 0.15 M salt in an aqueous medium) improves the adhesion of the gel formulation compared to that in a high ionic strength medium (e.g., aqueous solution with 0.15 M salt or greater). In some forms, a gel formulation in water adheres to a charged surface at a density of at least about 10, 13, 15, 17, 20, or 25 μg of gel/cm$^2$ of the surface, or greater, after extensive washing of the surface, whereas a gel formulation with a similar amount of gelator concentration but in phosphate buffered saline or solution with a higher salt concentration only adheres to a charged surface at less than about 5, 4, 3, 2, or 1 μg of gel/cm$^2$ of the surface, after extensive washing of the surface.

The gel composition with a high loading of amine-containing compounds (e.g., anesthetic agents and optionally anti-infectives and/or anti-inflammatories), in a formulation for adhesion to charged surfaces, can be administered in a patient locally or systemically, where the gel formulation adheres to an inflamed tissue or a pathological environment with a high amount of enzyme activity to provide release of the agents to alleviate or treat one or more symptoms of an disorder or disease.

DETAILED DESCRIPTION OF THE INVENTION

I. Definitions

Figure 1:
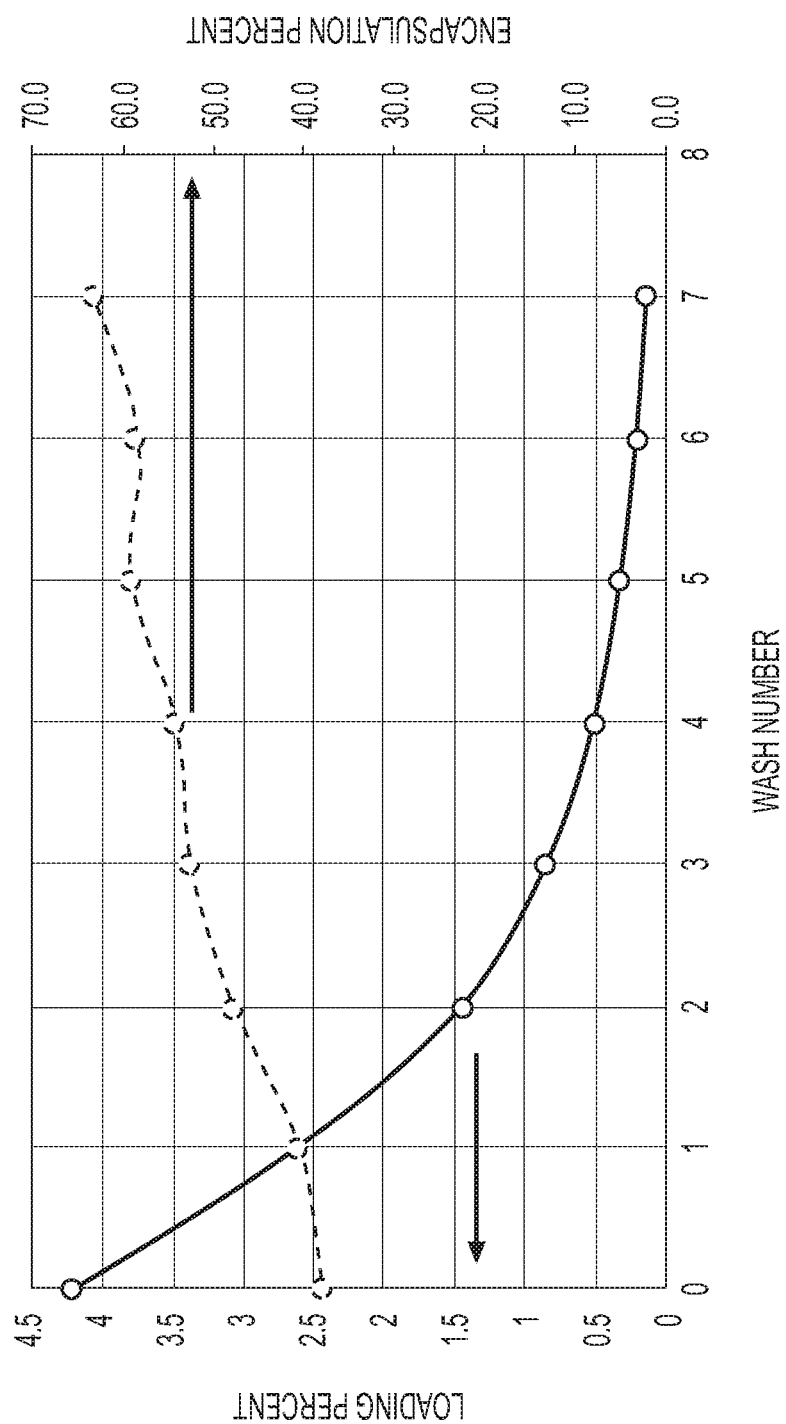
FIG. 1 is a line graph showing the loading percentage (mg lidocaine/mg total of solids [lidocaine and ascorbyl palmitate]) in the left Y-axis and the lidocaine encapsulation percentage in the right Y-axis over the number of washes in a centrifugation and resuspension process.
Figure 2A:
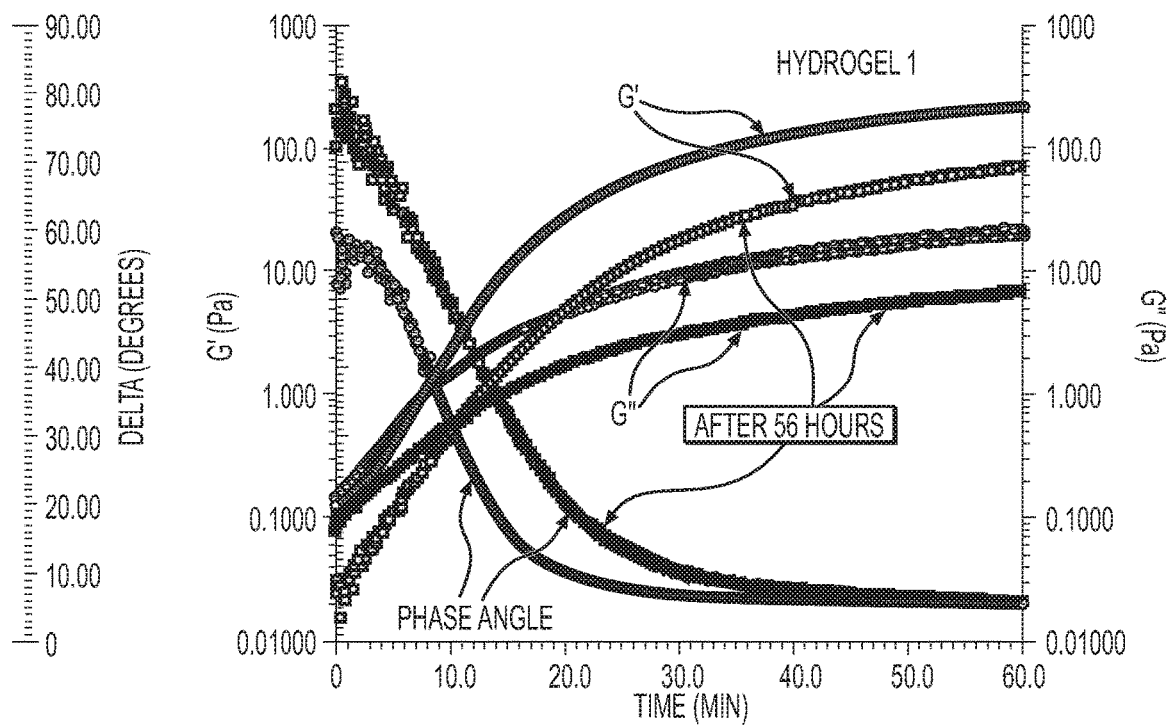
FIGS. 2A-2E are graphs showing the storage modulus G', loss modulus G", and phase angle data of hydrogels 1-5, respectively, as prepared in Example 6.
Figure 2B:
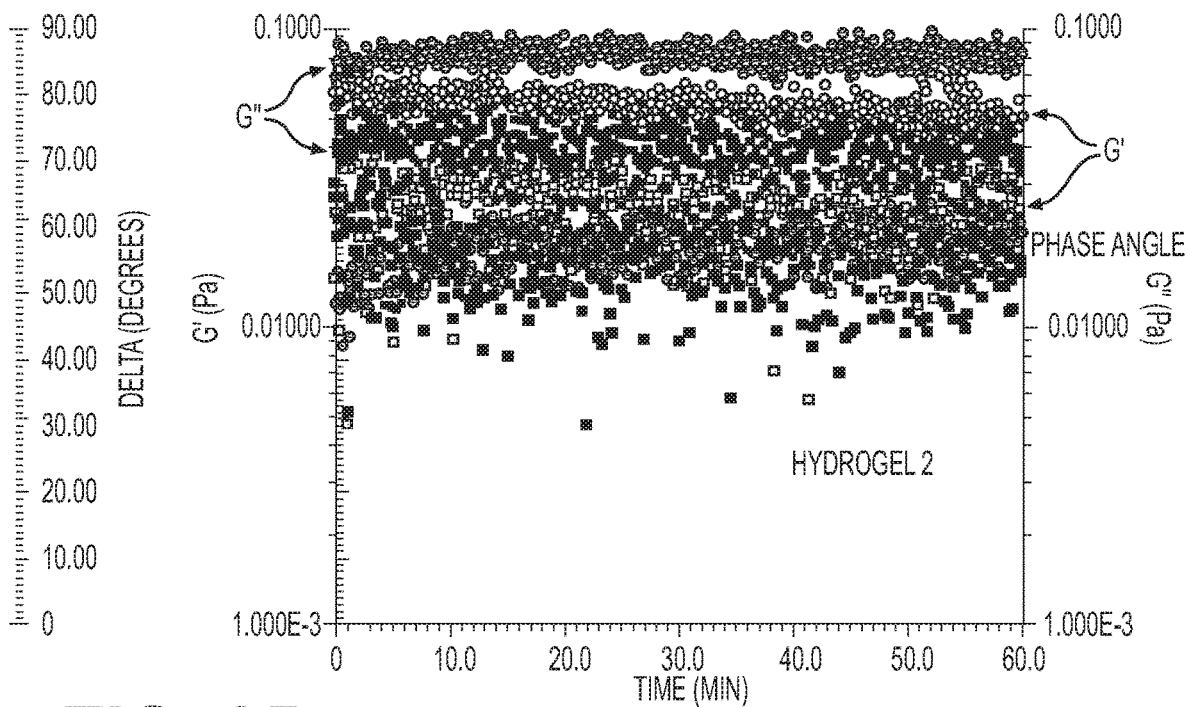
Figure 2C:
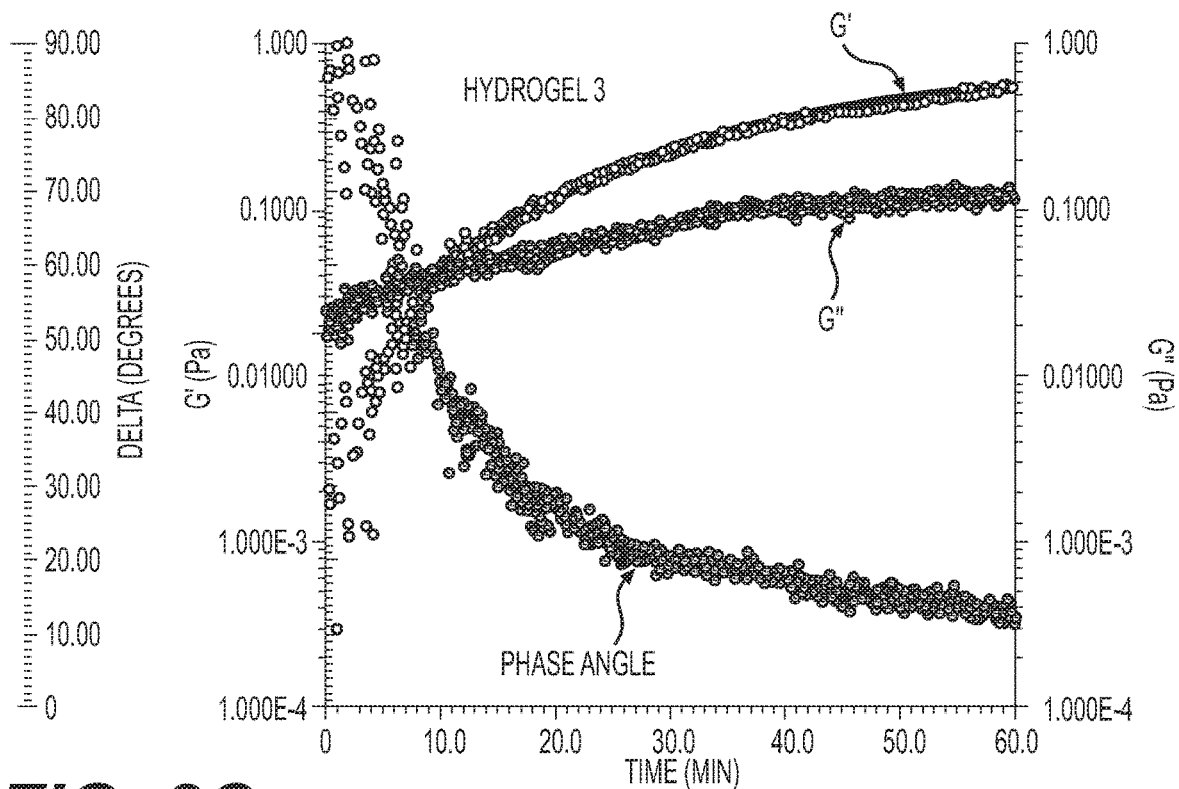
Figure 2D:
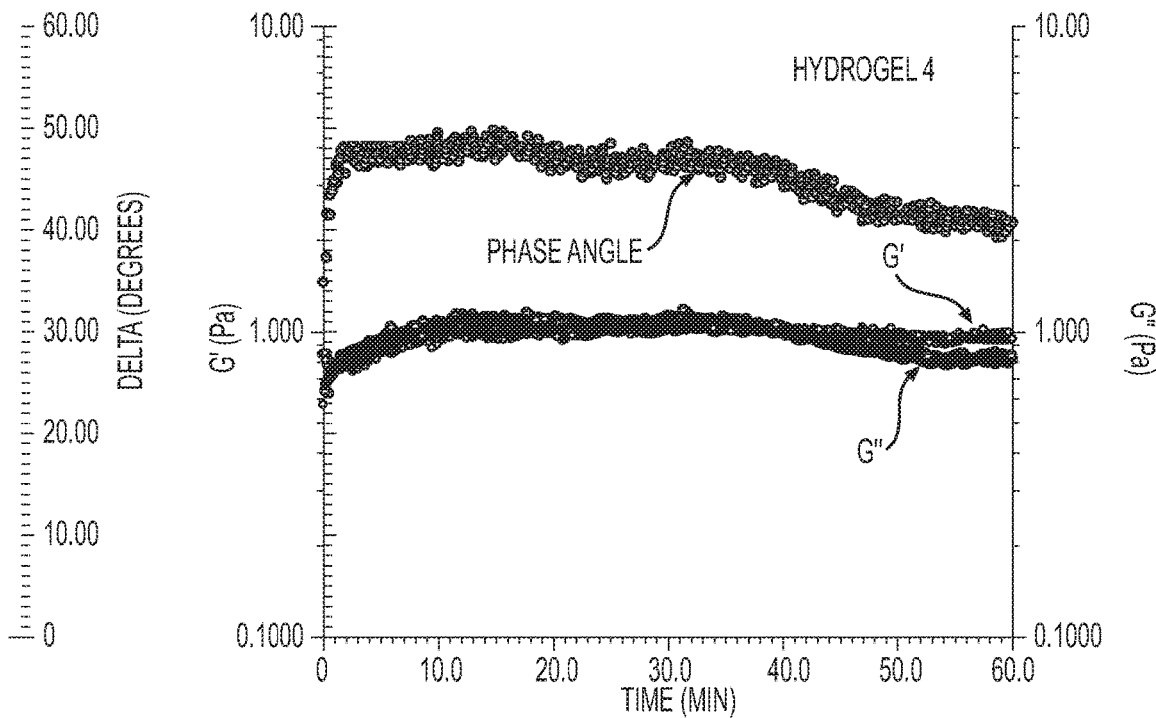
Figure 2E:
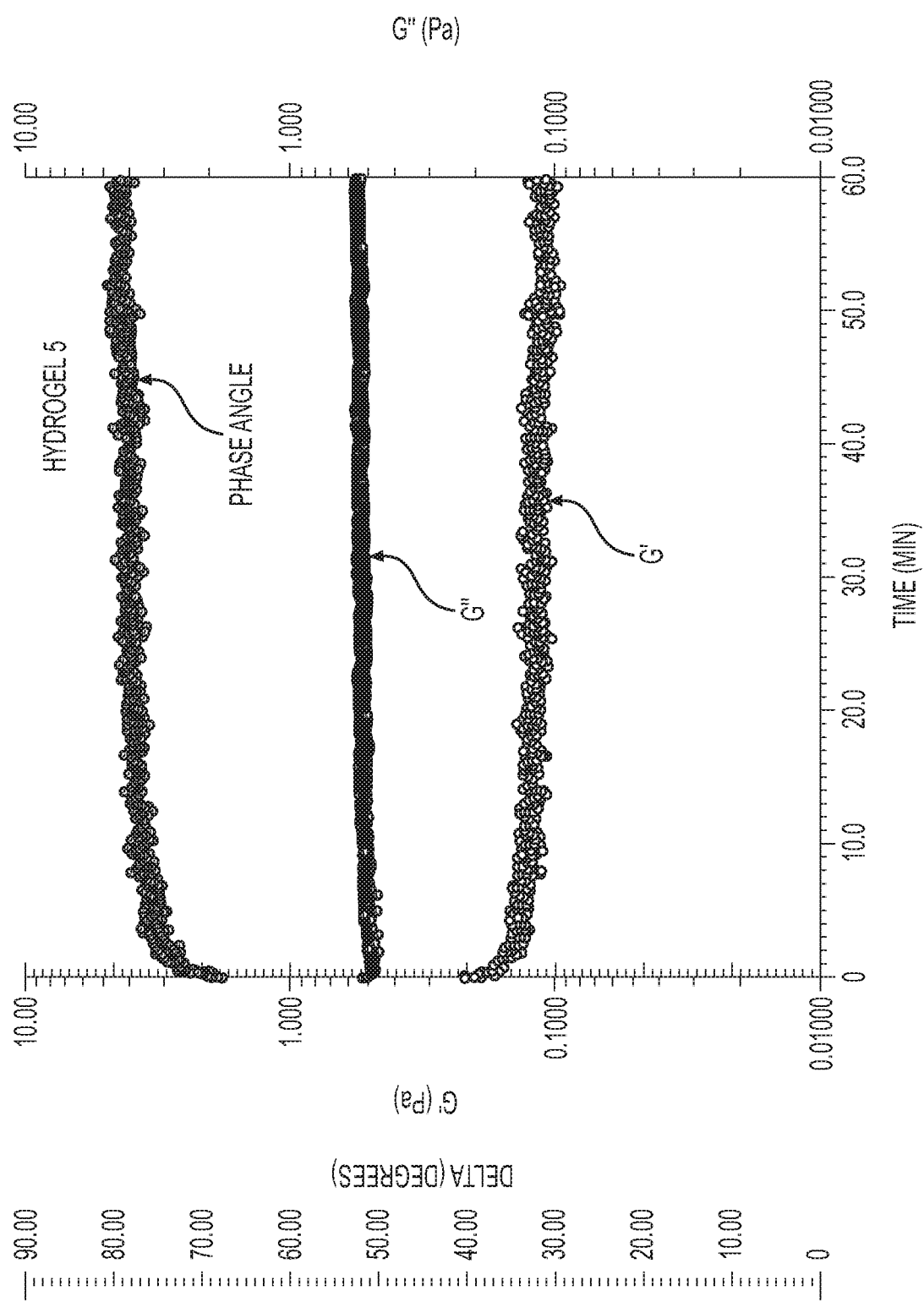

The term "loading" or "drug loading (DL)" is generally calculated as DL (%)=weight of encapsulated and/or associated drug (agent)÷weight of total of drug (agent) and gelator×100%.

The term "percent (%) encapsulated" or "encapsulation percentage" is generally calculated as % encapsulated=weight of encapsulated drug (agent)÷weight of total of drug (agent) measured (encapsulated+unencapsulated)×100%.

The term "encapsulation efficiency (EE)" is generally calculated as EE (%)=experimental/measured drug (agent) loading÷theoretical drug (agent) loading×100%.

The term "gelators" refer to molecules that can self-assemble through non-covalent interactions, such as hydrogen-bonding, van der Waals interactions, hydrophobic interactions, ionic interactions, pi-pi stacking, or combinations thereof, in one or more solvents. Gelators can include hydrogelators (e.g., gelators that form hydrogels) and organo-gelators (e.g., gelators that form organo-gels). In some embodiments, gelators can form either hydrogels or organo-gels. Typically gelators are amphiphilic.

The term "self-assembling" refers to the capability of molecules to spontaneous assemble, or organize, to form a high ordered structure such as hydrogel or organo-gel in a suitable environment.

The term "hydrogel" refers to three-dimensional (3-D) networks of molecules covalently (e.g., polymeric hydrogels) or non-covalently (e.g., self-assembled hydrogels) held together where water is the major component. Gels can be formed via self-assembly of gelators or via chemical cross-linking of gelators. Water-based gelators can be used to form hydrogels. Organo-gelators are gelators that form gels (organogels) in solvents where organic solvents are the major component.

The term "organo-gel" refers to 3-D networks of molecules covalently (e.g., polymeric hydrogels) or non-covalently (e.g., self-assembled hydrogels) held together where an organic solvent is the major component. Gels can be formed via self-assembly of gelators or via chemical cross-linking of gelators.

The term "therapeutic agent" refers to an agent that can be administered to prevent or treat one or more symptoms of a disease or disorder or dysfunction.

The term "diagnostic agent" generally refers to an agent that can be administered for purposes of identification or imaging.

The term "prophylactic agent" generally refers to an agent that can be administered to prevent disease or to prevent certain conditions like pregnancy.

The term "prodrug" refers to a drug, drug precursor of modified drug that is not fully active or available until converted in vivo or in situ to its therapeutically active or available form.

The term "adhere" as used herein refers to a gel composition sticks to a surface or substance following contact or incubation for some time. A mild wash solution generally does not remove the adhered gel composition from the surface. This mild wash solution includes the solvent or medium in which the gel composition is formed. A strong wash solution may remove the adhered gel composition from the surface, and the amount of adhered gel composition may be quantified therefrom. For a hydrogel formed in an aqueous medium, a strong wash solution to remove gel from an adherent surface includes an organic solvent, e.g., ethanol.

The term "organic solvent" refers to any carbon-containing substance that, in its liquid phase, is capable of dissolving a solid substance. Exemplary organic solvents commonly used in organic chemistry include toluene, tetrahydrofuran, acetone, dichloromethane, and hexane.

The term "water-miscible" refers to a solvent that mixes with water, in all proportions, to form a single homogenous liquid phase. This includes solvents like dimethyl sulfoxide (DMSO), tetrahydrofuran, acetone, ethanol, methanol, and dioxane, but generally excludes solvents such as hexane, oils, and ether. It also excludes solvents that have some, very limited miscibility or solubility in water such as ethyl acetate and dichloromethane, which are practically considered immiscible. Generally between about 20% and 50% by volume of a water-miscible organic solvent is used to make the hydrogels, with the balance being water or a buffer.

The term "salt" generally refers to an ionic compound formed by the reaction or neutralization of an acid with a base. Exemplary salts include pharmaceutically acceptable small molecules such as sodium chloride, potassium chloride, disodium phosphate, and monopotassium phosphate. This definition also includes a buffer salt as well (e.g., monosodium phosphate, disodium phosphate).

The term "amine" refers to compounds and functional groups that contain a basic nitrogen atom with a lone pair of electrons. This includes primary amines

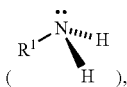

secondary amines

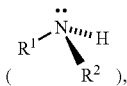

tertiary amines

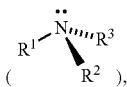

cyclic amines, and quaternary amines. Quaternary amines are usually quaternary ammonium cations

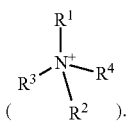

"Rheology" or "rheological property" as generally used herein refers to the properties related to deformation and flow of matter, such as a gel or fluid.

"Thixotropic" as generally used herein refers to a property of gels and/or fluids which show a time dependent response to shear. When subjected to a fixed shear rate, they will decrease in viscosity over time. Often this is observed as a large initial viscosity loss, followed by gradual further loss. Once shear is removed, thixotropic gels and/or fluids recover viscosity. These gels and/or fluids can also be considered pseudoplastic but only in that they demonstrate decreasing viscosity in response to increasing shear rate. Pseudoplasticity is commonly considered simply shear-thinning. More specifically, decreasing viscosity in response to increasing shear rate. Moreover, they immediately recover their non-sheared viscosity once shear is removed.

Numerical ranges include, but are not limited to, ranges of temperatures, ranges of concentrations (such as by weight, by volume, etc.), ranges of molecular weights, ranges of integers, and ranges of times, etc. The ranges include sub-ranges and combinations of sub-ranges encompassed therein. Use of the term "about" is intended to describe values either above or below the stated value, which the term "about" modifies, in a range of approx. +/−10%; in other instances the values may range in value either above or below the stated value in a range of approx. +/−5%. When the term "about" is used before a range of numbers (i.e., about 1-5) or before a series of numbers (i.e., about 1, 2, 3, 4, etc.) it is intended to modify both ends of the range of numbers or each of the numbers in the series, unless specified otherwise.

II. Composition

1. Gelator

Gelators are amphiphilic molecules which self-assemble to form gel compositions with nanofibrous structures. In a preferred embodiment, these are GRAS materials less than 2,500 Da in molecular weights.

Exemplary GRAS gelators include ascorbyl alkanoate, sorbitan alkanoate, triglycerol monoalkanoate, sucrose alkanoate, glycocholic acid, or any combination thereof. The alkanoate can include a hydrophobic $C_1$-$C_{22}$ alkyl (e.g., acetyl, ethyl, propyl, butyl, pentyl, caprylyl, capryl, lauryl, myristyl, palmityl, stearyl, arachidyl, or behenyl) bonded via a labile linkage (e.g., an ester, a carbamate, a thioester and an amide linkage) to an ascorbyl, sorbitan, triglycerol, or sucrose molecule. For example, the ascorbyl alkanoate can include ascorbyl palmitate, ascorbyl decanoate, ascorbyl laurate, ascorbyl caprylate, ascorbyl myristate, ascorbyl oleate, or any combination thereof. The sorbitan alkanoate can include sorbitan monostearate, sorbitan decanoate, sorbitan laurate, sorbitan caprylate, sorbitan myristate, sorbitan oleate, or any combination thereof. The triglycerol monoalkanoate can include triglycerol monopalmitate, triglycerol monodecanoate, triglycerol monolaurate, triglycerol monocaprylate, triglycerol monomyristate, triglycerol monostearate, triglycerol monooleate, or any combination thereof. The sucrose alkanoate can include sucrose palmitate, sucrose decanoate, sucrose laurate, sucrose caprylate, sucrose myristate, sucrose oleate, or any combination thereof. In some embodiments, the GRAS gelators include ascorbyl palmitate, sorbitan monostearate, triglycerol monopalmitate, sucrose palmitate, or glycocholic acid.

Representative low molecular weight GRAS gelators include vitamin precursors such as ascorbyl palmitate (vitamin C precursor), retinyl acetate (vitamin A precursor), and alpha-tocopherol acetate (vitamin E precursor).

In some embodiments, instead of or in addition to a GRAS first gelator, the self-assembled gel compositions are formed of amphiphilic 3-aminobenzamide derivatives having a molecular weight of 2,500 or less. The gelator can also be or include a prodrug that can transform to the active form of the drug in physiological conditions.

In other embodiments, one or more saturated or unsaturated hydrocarbon chains having $C_1$ to $C_{30}$ groups are synthetically modified onto a low molecular weight, generally hydrophilic compound, through esterification or a carbamate, anhydride, and/or amide linkage. The range $C_1$ to $C_{30}$ includes $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$ etc. up to $C_{30}$ as wells as ranges falling within $C_1$ to $C_{30}$, for example, $C_1$ to $C_{29}$, $C_2$ to $C_{30}$, $C_3$ to $C_{28}$, etc.

In some embodiments, alpha tocopherol acetate, retinyl acetate, retinyl palmitate, or a combination thereof, can co-assemble with the gelators.

2. Degradable Linkages

The gelators may release a therapeutic agent in response to a stimulus. Exemplary stimuli include ultrasound, temperature, pH, metal ions, light, electrical stimuli, electromagnetic stimuli, and combinations thereof. Stimuli evoking release can be present due to the characteristics at the site of administration or where release is desired, for example, tumors or areas of infection, commonly associated with low pH. These may be conditions present in the blood or serum, or conditions present inside or outside the cells, tissue or organ. The gel compositions may be designed to disassemble only under conditions present in a disease state of a cell, tissue or organ, e.g., inflammation, thus allowing for release of an agent at targeted tissue and/or organ.

In some embodiments, the gel compositions include degradable linkages that are cleavable upon contact with an enzyme and/or through hydrolysis, such as ester, amide, anhydride, a thioester, and carbamate linkages. Typically, linkage are between hydrophilic and hydrophobic parts of the amphiphile molecule. In some embodiments, phosphate-based linkages can be cleaved by phosphatases. In some embodiments, labile linkages are redox cleavable and are cleaved upon reduction or oxidation (e.g., —S—S—). In some embodiments, degradable linkages are susceptible to temperature, for example cleavable at high temperature, e.g., cleavable in the temperature range of 37-100° C., 40-100° C., 45-100° C., 50-100° C., 60-100° C., 70-100° C. In some embodiments, degradable linkages can be cleaved at physiological temperatures (e.g., from 36 to 40° C., about 36° C., about 37° C., about 38° C., about 39° C., about 40° C.). For example, linkages can be cleaved by an increase in temperature.

Selection of degradable linkages can result in lower dosages, because agents are only released at the required site. Another benefit is lowering of toxicity to other organs and tissues.

3. Liquid Medium for Gelation (Solvents and Buffer)

The gel is formed from the self-assembly and/or non-covalent interactions of a generally recognized as safe (GRAS) amphiphilic gelator and one or more therapeutic, prophylactic, or diagnostic agents encapsulated in the gel. In some forms, the gelator has a molecular weight of 2,500 or less, and is an ascorbyl alkanoate, a sorbitan alkanoate, a triglycerol monoalkanoate, or a sucrose alkanoate. Self-assembled gel is formed in a liquid medium such as distilled water, de-ionized water, pure or ultrapure water, saline, or other physiologically acceptable aqueous solutions containing salts (e.g., at between greater than 0 and 0.15 M NaCl; or between 10 mM and 500 mM), or a two-solvent system including an organic solvent and water (or an aqueous salt solution). Exemplary organic solvents include dimethyl sulfoxide (DMSO), methanol, acetone, ethanol, dioxane, acetonitrile, toluene, tetrahydrofuran, isobutyl alcohol, polyethylene glycol at a low molecular weight (e.g., 1 kDa) which is liquid at 37° C., propylene glycol, and dipropylene glycol.

Generally an organic solvent is mixed with and at least partially dissolves one or more gelators. Depending on the hydrophobicity or hydrophilicity, the amine-containing compounds may be dissolved in the co-solvent mixture or the aqueous solution which is then added to the gelator in the organic solvent. In a first embodiment, the agent is added to gelator dissolved in a co-solvent medium including both water (or an aqueous buffer or salt solution) and a water-miscible organic solvent with mixing and optionally heating to insure complete dissolution. In a second embodiment demonstrated in the examples, the gelators are dissolved initially in an organic solvent to form a solution with the gelators as the solutes (termed "gelator solution"). The agent, for example, free base lidocaine, is then dissolved in the gelator solution. An aqueous solution such as pure water or an aqueous buffer or salt solution is then mixed with the drug-gelator solution to form a liquid gel solution. The amount of the organic solvent in the total amount of liquid (organic+water/aqueous solution) is generally no more than 50%. If needed, the liquid gel solution is heated to insure complete dissolution, then cooled to form a gel stable to inversion at room temperature (25° C.) or body temperature (37° C.). Agent is added to form a final concentration in the gel of between about 4 and 25 wt/%. The amount of the organic solvent is generally between about 5% to about 50% by volume in the combined amount of the organic solvent and water (or an aqueous solution). Even if a higher % amount of the organic solvent is present in the gelator solution, most of the organic solvent in a self-assembled gel can be removed and replaced with media in purification techniques such as dialysis, centrifugation, and filtration.

Salt or buffer aqueous solutions may increase agent loading. For example, dissolving amphiphilic gelators in DMSO, then adding phosphate buffered saline (PBS) at a physiological ionic strength increases loading of amine-containing compounds in the resulting self-assembled gel, compared to water. As demonstrated in the example, inclusion of PBS increased loading of the amine-containing agent such as lidocaine or lidocaine hydrochloride to at least 4%, 6%, 8%, 10%, 15%, or 18% by weight, or greater in a gel formed in a DMSO-PBS system, whereas ultrapure water or water with essentially no salt formed a gel in a DMSO-water system encapsulating less than 0.5%, 1%, 2%, or 3% by weight of lidocaine or salts thereof.

In some instances, the inclusion of salt(s) during formation of gel, such as by adding salt(s) to buffer aqueous solutions can be used to tune the rheological properties of the gel, such as to impart thixotropy. For example, dissolving amphiphilic gelators in an organic solvent, such as DMSO, and adding phosphate buffered saline (PBS) containing one or more salts imparts thixotropic properties to the self-assembled gel, as compared to using water or a buffer solution without additional salt(s). Exemplary salts which can be added to tune the rheological properties of the gels include, but are not limited to sodium chloride, potassium chloride, calcium chloride, magnesium chloride, zinc chloride, or combinations thereof. Any suitable salt can be used that can provide sodium, potassium, calcium, magnesium, or zinc ions. In some instances, the salt(s) are added during gel formation. In some other instances, the salt(s) are added post-gel formation, such as during a post-processing step. The concentration of salt used (added during gel formation or in post-processing) to tune the rheological properties can be in the range of between about 0.1 to about 300 mM, about 0.1 to about 300 mM, about 0.1 to about 250 mM, about 0.1 to about 200 mM, about 0.1 to about 150 mM, about 0.1 to about 100 mM, about 0.1 to about 50 mM, or about 0.1 to about 25 mM. In some instances, the salts described here are added to buffer(s), such as a phosphate buffer, used to prepare the gels or in which a prepared gel may be resuspended in at concentrations ranging from between about 1 to 250 mM, about 1 to 200 mM, about 1 to 150 mM, about 1 to 100 mM, about 1 to 75 mM, about 1 to 50 mM, or about 1 to 25 mM. In some other instances, the salt(s) described here are added to buffer(s), such as a phosphate buffer, used to prepare the gels or in which a prepared gel may be resuspended in at concentrations of about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150 mM, or higher. The concentration of the one or more salts in the final gels after all processing steps may be at concentrations of about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150 mM, or higher.

In some instances, the inclusion of organic solvent(s) during formation of gel or added post-gel formation, such as during a post-processing step cam be used to tune the rheological properties of the gel, such as to impart thixotropy. Exemplary organic solvents which can be used, either alone or in combination with the salt(s) already discussed, to tune the rheological properties of the gels include, but are not limited to dimethylsulfoxide (DMSO), alcohols (such as methanol, ethanol, isopropanol, t-butanol). In some other instances, the organic solvent(s) described here are added as part of gel formation or can be added to buffer(s), such as a phosphate buffer, in which a prepared gel may be resuspended to provide gels with concentrations of organic solvent(s) of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, or 25% (volume/volume of total gel).

In yet other instances, a combination of salt(s) and organic solvent(s) as described immediately above can be used to tune the rheological properties of the gel, such as to impart thixotropy.

In some embodiments where gels are formed in a two-solvent system (e.g., in a DMSO-PBS system), increasing the proportion of the organic solvent relative to the aqueous salt solution results in an increase in the loading and encapsulation efficiency of amine-containing agents. Increasing the volume ratio of an organic solvent (e.g., DMSO) to an aqueous salt solution (e.g., phosphate-buffered saline) from 1:4 to 1:1 resulted in an increase of agent loading such as lidocaine loading in the self-assembled gel.

In other embodiments where amphiphilic gelators are first dissolved in an organic solvent, such as an alcohol (i.e., methanol), increasing the amount of salt in an aqueous phase to add to the alcohol-containing solution for gelation upon heating and cooling results in a decrease in the agent loading and encapsulation percentages.

The gel formulation can be further process to remove solvent, solvent impurities, excess agent (i.e., drug or free drug), for example, using dialysis, centrifugation, and/or filtration (e.g., tangential flow filtration (TFF)). In a preferred embodiment, solvent residue is removed to less than 1%, 3%, 5%, or 10% of the starting levels, or to less than the acceptance criteria of residual solvents of an organic solvent by U.S. Pharmacopeia Convention, International Conference on Harmonization guidance, or by U.S. Food and Drug Administration). The residual amount of solvent, solvent impurities, and/or excess drug or free drug which is not otherwise encapsulated or entrapped can be reduced to less than about 1,000 ppm, less than about 900 ppm, less than about 800 ppm, less than about 700 ppm, less than about 600 ppm, less than about 500 ppm, less than about 400 ppm, less than about 300 ppm, less than about 200 ppm, less than about 100 ppm less than about 50 ppm, or less. In some forms, dialysis or TFF in an aqueous medium with zero to less than 0.15 M salt effectively retains a greater amount of agent and maintains the high agent loading in a hydrogel as compared to dialysis in an aqueous medium with 0.15 M or a greater amount of salt.

Following formation of a self-supporting gel that is consistent, homogeneous, and stable to inversion, the gel may be suspended or purified in a pharmaceutically acceptable carrier to generate a desired volume for administration. Water or an aqueous medium with a low concentration of salt (e.g., less than 0.15 M) as the medium for suspension of the drug-loaded gel maintains the high loading content of the agent to at least 80%, 85%, 90%, 95%, or about 100% compared to the hydrogel composition before suspension; whereas phosphate buffered saline or aqueous medium containing about 0.15 M salt maintains about 65%, 70%, 75%, or 80% of the encapsulated agent content compared to before suspension. Suspension of a gel composition can provide a desired final volume of the formulation for ease of administration (e.g., for ease of administration to a patient in need thereof by drinking or injection) and/or a desired agent concentration to control toxicity. The gel can also be dried or lyophilized to remove all solvent, administered in dried form, or rehydrated for administration. Although the self-assembled gel is stable to inversion, i.e., it does not flow when inverted at ambient temperature (e.g., below the Krafft point of gelator) and pressure. The suspended gel in a pharmaceutically acceptable carrier may flow due to gravity.

In some embodiments the gel is suspended in a pharmaceutically acceptable carrier and then the gel dispersed or broken to form fibers or particles. Dispersion techniques include agitation, vortexing, pipetting, and homogenizing.

The gel formulation with a high loading content of amine-containing compounds (e.g., a self-supporting gel, a fibrous gel in the suspension medium, and a purified gel) adheres to a charged surface, such as those with amine functional groups on the surface. A lower or no ionic strength (e.g., zero to less than 0.15 M salt in an aqueous medium) improves the adhesion of the gel formulation compared to that in a high ionic strength environment (e.g., aqueous solution with 0.15 M salt or greater). In some forms, a gel formulation in water adheres to a charged surface at a density of at least about 10, 13, 15, 17, 20, or 25 µg of gel/cm$^2$ of the surface, or greater, after extensive washing of the surface, whereas a gel formulation with a similar amount of gelator concentration but in phosphate buffered saline or solution with a higher salt concentration only adheres to a charged surface at less than about 5, 4, 3, 2, or 1 µg of gel/cm$^2$ of the surface, after extensive washing of the surface.

As noted above, generally an organic solvent dissolves one or more gelators with or without heating. Depending on the hydrophobicity or hydrophilicity, the amine-containing compounds may be dissolved in the gelator solution in the organic solvent, or be dissolved with water or in an aqueous buffer solution which is added to the gelator solution in the organic solvent. The amount of the organic solvent is generally between about 5% to about 50% by volume in the combined amount of the organic solvent and water (or an aqueous solution).

In some forms, the organic solvent is used to pre-dissolve gelator, and the pre-dissolved gelator solution is used to dissolve amine-containing agents such as free base lidocaine or other amine-containing anesthetics in their free base form. Increasing the volume percentage of the organic solvent in the total gelation medium generally improves the loading of the amine-containing compounds, as well as the consistency/homogeneity of assembled gels (e.g., unlike flowable gels when inverted; also unlike gel-liquid mixtures where a top-layer liquid is present with the gel).

Suitable organic solvents include water-miscible solvent, or solvent that has an appreciable water solubility (e.g., greater than 5 g/100 g water), e.g., DMSO, acetone, dimethylformamide (DMF), tetrahydrofuran, dioxane, acetonitrile, and alcohol such as ethanol, methanol or isopropyl alcohol, and other water-miscible organic solvents, as well as low molecular weight polyethylene glycol (e.g., 1 kD PEG which melts at 37° C.).

The organic solution containing gelators and amine-containing compounds is further added to an amount of aqueous medium (e.g., saline) to undergo heat treatment to yield a self-assembled hydrogel that is stable to inversion (e.g., would not flow when contained in an inverted vial; aqueous component at least 50% in the medium to form a hydrogel) at room temperature. Generally, the amount of an organic solvent, if needed, to initially dissolve the gelator and/or agents is no more than equal volume or ½, ⅓, ¼, ⅕, ⅙, 1/7, ⅛, ⅑, 1/10, or less in volume compared to the volume of an aqueous medium to mix with the dissolved gelator and/or agents and to heat for hydrogel assembly. That is, the volume amount of an organic solvent in the total amount of liquid as used in forming a homogenous gel with high agent loading is generally no more than about 50%, 33%, 25%, 20%, 17%, 14%, 12.5%, 11%, 10%, or 9%.

In a preferred embodiment, between about 20% and 50% by volume of a water-miscible organic solvent is used to make the hydrogels, with the balance being water or a buffer; and a higher volume % of water-miscible organic solvent generally improves agent loading and gel consistency (e.g., lower % solvent can sometimes form flowable gels that would fail an inversion test).

The amount of the organic solvent in the self-assembled hydrogel can be substantially removed via dialysis, centrifugation, and/or filtration to yield suitable gel formulation still with high agent loading for administration. The residual amount of organic solvent can be reduced to less than about 1,000 ppm, less than about 900 ppm, less than about 800 ppm, less than about 700 ppm, less than about 600 ppm, less than about 500 ppm, less than about 400 ppm, less than about 300 ppm, less than about 200 ppm, less than about 100 ppm less than about 50 ppm, or less. Any residual amount of the organic solvent is generally within the stated limit of pharmaceutical products by the U.S. FDA, e.g., dichloromethane is below 600 ppm, methanol below 3,000 ppm, chloroform below 60 ppm, and within the limit by GMP or other quality based requirements. In some embodiments, aqueous solutions containing salts improves the loading amount of an agent in the gelator by dissolving both materials at once in the hydrogel assembly process. This is demonstrated in Example 1 where DMSO dissolves a gelator prior to the addition of phosphate buffered saline to form a homogeneous mixture which forms gel following heating and cooling.

In other embodiments, where a mixture of an aqueous buffer and an organic solvent is the medium for gel formation, increasing the amount of salts decreases the loading and encapsulation efficiency of an agent. This is demonstrated in Example 5 where methanol dissolves a gelator prior to the addition of an aqueous solution to form a homogeneous mixture which forms gel following heating and cooling.

Salts include pharmaceutically acceptable small molecules such as sodium chloride, potassium chloride, disodium phosphate, and monopotassium phosphate.

4. Amine-Containing Agents

The assembled gel compositions can be used to deliver one or more amine-containing agents to an individual or subject in need thereof, especially amine-containing anesthetic compounds.

It is believed that for lidocaine or other "-caine" anesthetic agents, and/or other aliphatic amine containing agents, that encapsulation can be challenging because self-assembled gels, such as those described herein, rely on hydrophobic moieties on the agents (i.e., drugs) to be encapsulated/entrapped in order to facilitate favorable encapsulation into the self-assembled gel. Previous attempts to address this challenge included creating hydrophobic prodrugs of hydrophilic agents that are otherwise not suitable for encapsulation into (hydro)gels (US2011/0229565 A1; Karp et. al. *Science Translational Medicine* 2015, 7(300): 300ra128). Such prior approaches, however, are limited to drugs and/or agents that contain chemical functionality amenable to conjugation to a hydrophobic moiety, such as palmitic acid, stearic acid, etc. via a cleavable linkage. Agents, such as lidocaine do not contain the required chemical functionality to utilize in a prodrug approach. In the gels and methods described herein, it is believed that electrostatic interactions between the acidic chemical functionality of the gelator(s) and the basic chemical functionality of the amine-containing agents (such as present in lidocaine in free base form) can facilitate encapsulation into the gel. Furthermore, it was found that inorganic salt and organic solvent present during the gel formulation and/or gel (post) processing can also affect the interaction between the gelator(s), such as ascorbyl palmitate, and the amine-containing agent, such as lidocaine. The type of salt and the salt concentration can be used to tune the encapsulation efficiency and correspondingly the extent of drug loading in the gel. There were no known methods prior to the methods described herein that could be used achieve tunable agent (drug) loading of an amine containing agent into self-assembled gel.

For self-assembled purified gel, a loading between about 5% and about 50% of amine-containing agent is significantly maintained even during a burst phase, e.g., no more than 25%, 30%, 40%, or 50% of the loaded agent is released at a burst phase, or virtually no burst release for concentrated systems at room temperature. This is unlike unpurified self-assembled materials by others which have very high burst release or even full release in a matter of minutes or hours.

In some embodiments, gelators may be prodrugs that hydrolytically or enzymatically degrade and release active agents.

In other embodiments, the amine-containing agent may be physically entrapped, encapsulated, or non-covalently associated with the nanofibrous structures of the gel composition. The agents may be covalently modified with one or more gelators, one or more stabilizers, or be used as a gelator. Alternatively, they are incorporated into the assembled ordered lamellar, vesicular, and/or nanofibrous structures of the gel composition or positioned on the surface of the assembled structures.

The self-assembled gels demonstrate loading efficiencies of the amine-containing agents (or other agents listed below) of up to about 90 wt/wt %, about 80 wt/wt %, about 70 wt/wt %, about 60 wt/wt %, about 50 wt/wt %, about 45 wt/wt %, about 40 wt/wt %, about 35 wt/wt %, about 30 wt/wt %, about 25 wt/wt %, about 20 wt/wt %, about 15 wt/wt %, about 10 wt/wt %, or about 5 wt/wt %.

The self-assembled gels demonstrate entrapment or encapsulation efficiencies of the amine-containing agents (or other agents listed below) of up to about 100 wt/wt %, 99 wt/wt %, 98 wt/wt %, 97 wt/wt %, 96 wt/wt %, 95 wt/wt %, 94 wt/wt %, 93 wt/wt %, 92 wt/wt %, 91 wt/wt %, 90 wt/wt %, about 80 wt/wt %, about 70 wt/wt %, about 60 wt/wt %, about 50 wt/wt %, about 45 wt/wt %, about 40 wt/wt %, about 35 wt/wt %, about 30 wt/wt %, about 25 wt/wt %, about 20 wt/wt %, about 15 wt/wt %, about 10 wt/wt %, or about 5 wt/wt %.

In some instances, the self-assembled gels are prepared with the inclusion of salt(s) and/or organic solvent(s) during formation of gel or added post-gel formation, such as during a post-processing step, in order to tune the rheological properties of the gel. In such instances where the rheological properties are tuned, such as to impart thixotropic properties to the gel, the amounts of salt(s) and/or organic solvent(s) used in preparing the gel is controlled to preferably obtain encapsulation efficiencies of at least about 50 wt/wt %, about 45 wt/wt %, about 40 wt/wt %, about 35 wt/wt %, about 30 wt/wt %, about 25 wt/wt %, about 20 wt/wt %, about 15 wt/wt %, about 10 wt/wt %, or about 5 wt/wt % in the gel.

Anesthetic Agents

In some embodiments, the amine-containing agents are anesthetic agents which are entrapped, encapsulated, embedded, electrostatically bound, or otherwise delivered in the gel matrix at a loading content of at least 4%, 5%, 6%, 7%, 8%, 9%, 10%, or greater; and these formulations maintain the high loading content of anesthetics even during post-formation processes such as suspension and purification. Generally, anesthetics are loaded at between about 5% and about 25% by weight in the gel matrix.

Most of the common local anesthetics (e.g., lidocaine, procaine, dibucaine, tetracaine, benzocaine, bupivacaine) contain ionizable tertiary amines, which can exist in two forms, i.e., an uncharged free base form (B) and a cationic form ($BH^+$), depending on the $pK_a$ value of the compound and the pH of the medium according to the Henderson-Hasselbach equation $$pKa = pH + \log_{10}([BH^+]/[B])$$

where [$BH^+$] and [B] represent the concentrations of the charged and uncharged forms, respectively. The form of the tertiary amine-containing anesthetics (e.g., lidocaine) may be responsible for nerve blocking. The uncharged free base form generally penetrates cell membranes and tissue much more easily than the charged form (Henry R, et al., *J Urol*, June; 165 (6 Pt 1): 1900-1903 (2001)). If the site of action is located on the internal surface of the nerve membrane, local anesthetic molecules need to pass through both the nerve sheath and the nerve membrane before exerting the blocking action. The charged form competes with sodium for the negative carrier sites in the sodium channel.

In some embodiments, the free base form of amine-containing agents are used in preparing the gel formulation and the gel can include both the free base and conjugate acid of the free base in equilibrium. For example, lidocaine has a loading content of at least 4% in the assembled gel matrix, e.g., between about 4% and about 18%. During gel suspension and purification processes, the loading content of the anesthetic remains at least 90%, 80%, or 70% compared to the loaded amount of anesthetic after gel assembly is complete.

In some embodiments, lidocaine, procaine, tetracaine, dibucaine, benzocaine, bupivacaine, or salts thereof, is included in the assembled gel formulation. For example, lidocaine hydrochloride, procaine hydrochloride, tetracaine hydrochloride, dibucaine hydrochloride, benzocaine hydrochloride, and/or bupivacaine may be used. Freebase lidocaine, procaine, tetracaine, benzocaine, bupivacaine, or dibucaine may also be mixed with gelator material and encapsulated in the assembled hydrogel in the presence of appropriate solvents.

In some instances, the gel formulation is also suitable for delivery of amine-containing agents, such as anesthetics and additional agents, such as antibiotics, anti-inflammatories, antimicrobials, or combinations thereof.

Antibiotics/Anti-Microbials

The gel formulation and self-assembly process for high agent loading is also suitable for delivering antibiotics and/or antimicrobials. In some forms, suitable antibiotic/antimicrobial agent compounds for high loading in the gel formulation include tetracyclines, doxycycline, minocycline, metacycline, demeclocycline, rolitetracycline, lymecycline, meclocycline, miocamycin, aminoglycosides, ansaycins, carbapenems, cephalosporins, glycopeptides, lincosamides, lipopeptides, macrolides, monobactams, nitrofurans, oxazolidinones, penicillins, polypeptides, quinolones/fluoroquinolone, sulfonamides, clofazimine, dapsone, capreomycin, cycloserine, ethambutol, ethionamide, isoniazid, pyrazinamide, rifampicin (rifampin), rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, and trimethoprim; and combinations thereof.

Anti-Inflammatories

The gel formulation and self-assembly process for high agent loading is also suitable for delivering anti-inflammatories such as steroids like cortisone and prednisone and/or non-steroidal anti-inflammatories, such as naproxen.

5. Optional Stabilizing Agent

In some embodiments, agents enhancing blood stability and/or reducing the rate of disassembly of nanostructures after administration are included in the composition. Blood proteins including albumin can interact with irregularities in the assembled lamellar, micellar, vesicular, and/or fibrous structures, such as those that exist at the phase boundaries, resulting in a higher rate of disassembly of particles or the higher structured nanoparticles or bulk hydrogel. Stabilizing agents typically impart rigidity, increase the packing density, and/or enhance the strength of assembled structures, thus altering the phase transition process and transitioning temperature, and/or modulating the surface properties of assembled particles to reduce or prevent protein adhesion or accumulation.

Generally, the stabilizing agents diminish the rate of reduction in the size of the assembled particles or nanoparticles when placed in a serum solution, whereas compositions without stabilizing agents substantially decrease the hydrodynamic size in serum solutions in about 30 minutes. Stabilizing agents allow for more than 50%, 60%, 70%, 80%, 90%, 95%, 99% of the assembled nanostructures to have less than 1%, 5%, 10%, 15%, 20%, or 30% reduction in the hydrodynamic sizes in at least one, two, three, four, 12, 24, or 48 hours in incubation with serum at 37° C.

In general, the molecules that can rigidify the self-assembled lamellae will usually be hydrophobic molecules, molecules that can change surface properties, like small chain hydrophilic polymers, and/or molecules that can modify the surface charge (charged molecules).

In some embodiments, the stabilizing agents are co-assembled with gelators in the formation of assembled gel compositions. These stabilizing agents are generally incorporated into the lamellar, micellar, vesicular, and/or fibrous structures by encapsulation, integrated, entrapment, insertion or intercalation. Generally, inclusion of 10-30 mole % of co-assembly type, stabilizing agents allows for the assembled nanoparticles to maintain about 80% or more of the original size when incubated over a period of two to four hours in serum solutions.

Exemplary stabilizing agents include sterols, phospholipids, and low molecular weight therapeutic compounds that are typically hydrophobic. Suitable sterols include cholesterol, corticosteriods such as dihydrocholesterol, lanosterol, β-sitosterol, campesterol, stigmasterol, brassicasterol, ergocasterol, Vitamin D, phytosterols, sitosterol, aldosterone, androsterone, testosterone, estrogen, ergocalciferol, ergosterol, estradiol-17alpha, estradiol-17beta, cholic acid, corticosterone, estriol, lanosterol, lithocholic acid, progesterone, cholecalciferol, cortisol, cortisone, cortisone acetate, cortisol acetate, deoxycorticosterone and estrone and fucosterol. Other stabilizing agents include, but are not limited to, lysophospholipids (including lyso PC, 2-hexadecoxy-oxido-phosphoryl)oxyethyl-trimethyl-azanium), gangliosides, including GM1 and GT1b, sulfatide, sphingophospholipids, synthetic glycopholipids such as sialo-lactosyl, phospholipids, including DOPE, DOPS, POPE, DPPE, DSPE, lipophilic drugs such as cytosine arabinoside diphosphate diacyglycerol, proteins such as cytochrome b5, human high density lipoprotein (HDL), human glycophorin A, short chain hydrophilic polymers, including polyethylene glycol (PEG) and their derivatives with lipids, bile acids include taurocholic acid, desoxycholic acid, and geicocholic acid, 1,1'-dioctadecyl 3,3,3',3'-tetramethyl-indocarbocyanine percholorate (DiI), DiR, DiD, fluorescein isothiocynate, tetramethylrhodamine isothiocyanate, rhodamine B octadecyl ester perchlorate and N'-Octadecylfuorescein-5-thiourea. Sterols generally co-assemble with one or more gelators, inserting into the ordered lamellar, micellar, vesicular, and/or fibrous structures. Sterols by themselves are not gelators and cannot form gel compositions on their own.

Suitable phospholipids include dipalmitoyl phosphatidyl choline and distearoyl phosphatidyl choline. The phospholipids typically co-assemble with one or more gelators in forming the ordered lamellar and/or fibrous structures.

In other embodiments, the stabilizing agents are an agent encapsulated in the assembled composition, typically throughout the gel composition, rather than insertion or intercalation into the lamellar, micellar, vesicular, and/or fibrous structures. Generally, inclusion of between 5 and 15 mole % stabilizing agents allows for the assembled nanostructures to maintain about 80% or more of the original size when incubated over a period of two to four hours in serum solutions.

In some embodiments, the agents may diminish reduction in the size of the assembled nanostructures when placed in a blood or serum solution, where more than 50%, 60%, 70%, 80%, 90%, 95%, 99% of the nanostructures in incubation with serum at 37° C. have less than 1%, 5%, 10%, 15%, 20%, or 30% reduction in the hydrodynamic sizes in at least one, two, three, four, 12, 24, or 48 hours, compared to gel composition without the active agents. A hydrophobic agent may stabilize the nanostructures formed from gelators when encapsulated at a molar percentage of 2%, 4%, 6%, 8%, and 10%, and all values in the range, between the active agent and the gelators.

Suitable low molecular weight therapeutic, prophylactic and/or diagnostic agents used as stabilizing agents for the gel compositions are generally hydrophobic, of a low molecular weight (e.g., less than 2,500 Da), such as docetaxel and steroids and other hydrophobic agents such as dexamethasone, or a combination of agents.

6. Formulations

The gel composition is formed generally by heating and mixing the gelator and the agent(s) in a medium to completely or near completely dissolve the gelator, followed by cooling to below the Krafft point to allow the assembly of the gelators around and/or having on the surface the agents. In some forms, an organic solvent (e.g., in a small amount generally less than about 1/10 compared to the amount of the aqueous medium) is used to dissolve the gelator with the agent(s) to form a homogenous solution, before the addition of an amount of an aqueous medium for heating and formation of a hydrogel composition.

A formed gel is generally stable to inversion, e.g., resist gravitational flow from a vial when the vial containing the gel is inverted to an upright or tilted position. A formed gel may also retain its structural presence and stay as applied without being washed away at 37° C. or in vivo. A formed gel may include nanostructures from the gelator or the gelator and the agents, where the nanostructures include lamellar structures, fibers, sheet-like structures, tape-like structures, nanoparticles, or combinations thereof.

The gel is formed from the self-assembly and/or non-covalent interactions of a generally recognized as safe (GRAS) amphiphilic gelator and one or more therapeutic, prophylactic, or diagnostic agents encapsulated in the gel. In some forms, the gelator has a molecular weight of 2,500 or less, and is an ascorbyl alkanoate, a sorbitan alkanoate, a triglycerol monoalkanoate, or a sucrose alkanoate. Self-assembled gel is formed in a liquid medium such as distilled water, de-ionized water, pure or ultrapure water, saline, or other physiologically acceptable aqueous solutions containing salts (e.g., at between greater than 0 and 0.15 M NaCl; or between 10 mM and 500 mM), or a two-solvent system including an organic solvent and water (or an aqueous salt solution). Exemplary organic solvents are dimethyl sulfoxide (DMSO), methanol, acetone, ethanol, dioxane, acetonitrile, toluene, tetrahydrofuran, isobutyl alcohol, polyethylene glycol at a low molecular weight (e.g., 1 kDa) which is liquid at 37° C., propylene glycol, dipropylene glycol, or combinations thereof.

Generally an organic solvent is mixed with and at least partially dissolves one or more gelators. Depending on the hydrophobicity or hydrophilicity, the amine-containing compounds may be dissolved in the co-solvent mixture or the aqueous solution which is then added to the gelator in the organic solvent. In a first embodiment, the agent is added to gelator dissolved in a co-solvent medium including both water (or an aqueous buffer or salt solution) and a water-miscible organic solvent with mixing and optionally heating to insure complete dissolution. In a second embodiment demonstrated in the examples, the gelators are dissolved initially in an organic solvent to form a solution with the gelators as the solutes (termed "gelator solution"). The agent, for example, free base lidocaine, is then dissolved in the gelator solution. An aqueous solution such as pure water or an aqueous buffer or salt solution is then mixed with the drug-gelator solution to form a liquid gel solution. The amount of the organic solvent in the total amount of liquid (organic+water/aqueous solution) is generally no more than 50%. If needed, the liquid gel solution is heated to insure complete dissolution, then cooled to form a gel stable to inversion at room temperature (25° C.) or body temperature (37° C.). Agent is added to form a final concentration in the gel of between about 4 and 25 wt/%. The amount of the organic solvent is generally between about 5% to about 50% by volume in the combined amount of the organic solvent and water (or an aqueous solution). Even if a higher % amount of the organic solvent is present in the gelator solution, most of the organic solvent in a self-assembled gel can be removed and replaced with media in purification techniques such as dialysis, centrifugation, and filtration.

Salt or buffer aqueous solutions may increase agent loading. For example, dissolving amphiphilic gelators in DMSO, then adding phosphate buffered saline (PBS) at a physiological ionic strength increases loading of amine-containing compounds in the resulting self-assembled gel, compared to water. As demonstrated in the example, inclusion of PBS increased loading of the amine-containing agent such as lidocaine or lidocaine hydrochloride to at least 4%, 6%, 8%, 10%, 15%, or 18% by weight, or greater in a gel formed in a DMSO-PBS system, whereas ultrapure water or water with essentially no salt formed a gel in a DMSO-water system encapsulating less than 0.5%, 1%, 2%, or 3% by weight of lidocaine or salts thereof.

In some instances, the inclusion of salt(s) during formation of gel, such as by adding salt(s) to buffer aqueous solutions, can be used to tune the rheological properties of the gel, such as to impart thixotropy. For example, dissolving amphiphilic gelators in an organic solvent, such as DMSO, and adding phosphate buffered saline (PBS) containing one or more salts imparts thixotropic properties to the self-assembled gel, as compared to using water or a buffer solution without additional salt(s). Exemplary salts which can be added to tune the rheological properties of the gels include, but are not limited to sodium chloride, potassium chloride, calcium chloride, magnesium chloride, zinc chloride, or combinations thereof. Any suitable salt can be used that can provide sodium, potassium, calcium, magnesium, or zinc ions. In some instances, the salt(s) are added during gel formation. In some other instances, the salt(s) are added post-gel formation, such as during a post-processing step. The concentration of salt used (added during gel formation or in post-processing) to tune the rheological properties can be in the range of between about 0.1 to about 300 mM, about 0.1 to about 300 mM, about 0.1 to about 250 mM, about 0.1 to about 200 mM, about 0.1 to about 150 mM, about 0.1 to about 100 mM, about 0.1 to about 501 M, or about 0.1 to about 25 mM. In some instances, the salts described here are added to buffer(s), such as a phosphate buffer, used to prepare the gels or in which a prepared gel may be resuspended in at concentrations ranging from between about 1 to 250 mM, about 1 to 200 mM, about 1 to 150 mM, about 1 to 100 mM, about 1 to 75 mM, about 1 to 50 mM, or about 1 to 25 mM. In some other instances, the salt(s) described here are added to buffer(s), such as a phosphate buffer, used to prepare the gels or in which a prepared gel may be resuspended in at concentrations of about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150 mM, or higher. The concentration of the one or more salts in the final gels after all processing steps may be at concentrations of about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150 mM, or higher.

In some instances, the inclusion of organic solvent(s) during formation of gel or added post-gel formation, such as during a post-processing step to tune the rheological properties of the gel, such as to impart thixotropy. Exemplary organic solvents which can be used, either alone or in combination with the salt(s) already discussed, to tune the rheological properties of the gels include, but are not limited to dimethylsulfoxide (DMSO), alcohols (such as methanol, ethanol, isopropanol, t-butanol). In some other instances, the organic solvent(s) described here are added as part of gel formation or can be added to buffer(s), such as a phosphate buffer, in which a prepared gel may be resuspended to provide gels with concentrations of organic solvent(s) of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, or 25% (volume/volume of total gel).

In yet other instances, a combination of salt(s) and organic solvent(s) as described immediately above can be used to tune the rheological properties of the gel, such as to impart thixotropy.

As shown in Example 6, at fixed gelator (such as ascorbyl palmitate) to agent (such as lidocaine) concentrations, the rheological properties can be notably altered by the inclusion of salt(s) and organic solvent(s) and their respective concentrations. It has been shown that self-assembled ascorbyl palmitate hydrogels have recoverable rheological properties, i.e. shear thinning (US2013/0280334 A1, US2017/0319500 A1). The inclusion of salt(s) and/or solvent(s) demonstrates that the rheological properties can be controlled or tuned without altering the concentration of gelator (such as ascorbyl palmitate) or agent (such as lidocaine) in the gel formulation. Control over rheological properties is an important invention because the viscosity and rheology of a locally administered therapeutic can affect its disposition to the tissue in question.

In some instances, the gels can be formed without any additional salts and/or organic solvents or their rheological properties can be tuned by addition of salts and/or organic solvent(s) (either during gel formation or post-gel formation). The gels described can have or can be tuned to have a storage modulus (G') of from about 0.1, from about 0.2, from about 0.3, from about 0.4, from about 0.5, from about 0.6, from about 0.7, from about 0.8, from about 0.9, from about 1, from about 2, from about 3, from about 4, or from about 5 Pascals up to about 50, about 75, about 100, about 150, about 200, about 250, or about 300, or any combination of upper and lower end points disclosed herein.

In some instances, the gels can be formed without any additional salts and/or organic solvents or their rheological properties can be tuned by addition of salts and/or organic solvent(s) (either during gel formation or post-gel formation). The gels described can have or can be tuned to have a loss modulus (G") of from about 0.1, from about 0.2, from about 0.3, from about 0.4, from about 0.5, from about 0.6, from about 0.7, from about 0.8, from about 0.9, from about 1, from about 2, from about 3, from about 4, or from about 5 Pascals up to about 10, about 15, about 20, about 25, about 30, about 35, about 40, or about 300 Pascals, or any combination of upper and lower end points disclosed herein.

In some instances, the gels formed with or without addition of salts and/or organic solvent(s) (either during gel formation or post-gel formation) have can have viscosities in a range from between about 0.1, from about 0.2, from about 0.3, from about 0.4, from about 0.5, from about 0.6, from about 0.7, from about 0.8, from about 0.9, from about 1, from about 2, from about 3, from about 4, or from about 5 centipoise (cP) up to about 10, about 100, about 200, about 300, about 400, about 500, about 600, about 700, about 800, about 900, about 1,000, about 1,100, about 1,200, about 1,300, about 1,400, about 1,500, about 1,600, about 1,700, about 1,800, about 1,900, about 2,000, about 2,500, or about 3000 cP, or any combination of upper and lower end points disclosed herein. In some instances, the gels formed addition of salts and/or organic solvent(s) (either during gel formation or post-gel formation) exhibit thixotropic properties such that the viscosity of the gel changes upon exposure to shear, for example.

In some embodiments where gels are formed in a two-solvent system (e.g., in a DMSO-PBS system), increasing the proportion of the organic solvent relative to the aqueous salt solution results in an increase in the loading and encapsulation efficiency of amine-containing agents. Increasing the volume ratio of an organic solvent (e.g., DMSO) to an aqueous salt solution (e.g., phosphate-buffered saline) from 1:5 to 1:1 resulted in an increase of agent loading such as lidocaine loading in the self-assembled gel.

In other embodiments where amphiphilic gelators are first dissolved in an organic solvent such as methanol, increasing the amount of salt in an aqueous phase to add to the methanol solution for gelation upon heating and cooling results in a decrease in the agent loading and encapsulation percentages.

The gel formulation can be further processed to remove solvent, solvent impurities, excess agent (i.e., drug or free drug), for example, using dialysis, centrifugation, and/or filtration (e.g., tangential flow filtration (TFF)). In a preferred embodiment, solvent residue is removed to less than 1%, 3%, 5%, or 10% of the starting levels, or to less than the acceptance criteria of residual solvents of an organic solvent by U.S. Pharmacopeia Convention or by U.S. Food and Drug Administration). The residual amount of solvent, solvent impurities, excess drug or free drug not otherwise encapsulated or entrapped by the gel, can be reduced to less than about 1,000 ppm, less than about 900 ppm, less than about 800 ppm, less than about 700 ppm, less than about 600 ppm, less than about 500 ppm, less than about 400 ppm, less than about 300 ppm, less than about 200 ppm, less than about 100 ppm less than about 50 ppm, or less. In some forms, dialysis or TFF in an aqueous medium with zero to less than 0.15 M salt effectively retains a greater amount of agent and maintains the high agent loading in a hydrogel as compared to dialysis in an aqueous medium with 0.15 M or a greater amount of salt.

Following formation of a self-supporting gel that is consistent, homogeneous, and stable to inversion (typically at room temperature) meaning no gravitational flow is observed in the gel upon inversion of the container holding the gel for at least 5, 10, or 15 seconds, and in some cases, for about 1, 5, 10, 30, or 60 minutes, 1 day, 2 days, 3 days, 1 week, 2 weeks, or longer. The gels preferably demonstrate stabilities of inversion of at least 60 minutes or longer. The gel may be suspended or purified in a pharmaceutically acceptable carrier to generate a desired volume for administration. Water or an aqueous medium with a low concentration of salt (e.g., less than 0.15 M) as the medium for suspension of the drug-loaded gel maintains the high loading content of the agent to at least 80%, 85%, 90%, 95%, or about 100% compared to the hydrogel composition before suspension; whereas phosphate buffered saline or aqueous medium containing about 0.15 M salt maintains about 65%, 70%, 75%, or 80% of the encapsulated agent content compared to before suspension. Suspension of a gel composition can provide a desired final volume of the formulation for ease of administration (e.g., for ease of administration to a patient in need thereof by drinking or injection) and/or a desired agent concentration to control toxicity. The gel can also be dried or lyophilized to remove all solvent, administered in dried form, or rehydrated for administration. Although the self-assembled gel is stable to inversion, i.e., it does not flow when inverted at ambient temperature (e.g., below the Krafft point of gelator) and pressure. Stability to inversion is typically determined at room temperature and is characterized by a resistance of the gel to gravitational flow for a period of time of at least 60 minutes or longer). The suspended gel in a pharmaceutically acceptable carrier may flow due to gravity.

In some embodiments the gel is suspended in a pharmaceutically acceptable carrier and then the gel dispersed or broken to form fibers or particles. Dispersion techniques include agitation, vortexing, pipetting, and homogenizing.

The gel formulation with a high loading content of amine-containing compounds (e.g., a self-supporting gel, a fibrous gel in the suspension medium, and a purified gel) adheres to a charged surface, such as those with amine functional groups on the surface. A lower or no ionic strength (e.g., zero to less than 0.15 M salt in an aqueous medium) improves the adhesion of the gel formulation compared to that in a high ionic strength environment (e.g., aqueous solution with 0.15 M salt or greater). In some forms, a gel formulation in water adheres to a charged surface at a density of at least about 10, 13, 15, 17, 20, or 25 µg of gel/cm$^2$ of the surface, or greater, whereas a gel formulation with a similar amount of gelator concentration but in phosphate buffered saline or solution with a higher salt concentration only adheres to a charged surface at less than about 5, 4, 3, 2, or 1 µg of gel/cm$^2$ of the surface.

Liquid Formulations to Suspend Agent-Loaded Gel

Liquid formulations contain self-assembled dispersed gel, nanostructures or combinations thereof suspended in a liquid pharmaceutical carrier. In some forms, self-assembled gel is suspended or resuspended in aqueous media for ease of administration and/or reaching a desired concentration for minimizing toxicity. In some forms, while a salt buffered substantially aqueous medium is preferred in forming self-assembled hydrogel with high agent loading content, water is preferred over salt solutions in gel suspension and purification steps for maintaining the high agent content.

Suitable liquid carriers include, but are not limited to, distilled water, de-ionized water, pure or ultrapure water, saline, and other physiologically acceptable aqueous solutions containing salts and/or buffers, such as phosphate buffered saline (PBS), Ringer's solution, and isotonic sodium chloride, or any other aqueous solution acceptable for administration to an animal or human. Preferably the concentration of salts therein is in a physiological range.

In some embodiments, distilled water, de-ionized water, pure or ultrapure water as a suspension medium and as a purification medium yields a higher loading amount of agents in the assembled hydrogel than PBS does or other salt solutions.

In other embodiments, the liquid formulations are isotonic relative to physiological fluids and of approximately the same pH, ranging from about pH 4.0 to about pH 8.0, more preferably from about pH 6.0 to pH 7.0. The pH is selected such that agent to be loaded, e.g., lidocaine, does not precipitate, as well as close to physiological conditions. The liquid pharmaceutical carrier can include one or more physiologically compatible buffers, such as a phosphate or bicarbonate buffers. One skilled in the art can readily determine a suitable saline content and pH for an aqueous solution that is suitable for an intended route of administration.

Liquid formulations may include one or more suspending agents, such as cellulose derivatives, sodium alginate, polyvinylpyrrolidone, gum tragacanth, or lecithin. Liquid formulations may also include one or more preservatives, such as ethyl or n-propyl p-hydroxybenzoate.

Formulations may be prepared using one or more pharmaceutically acceptable excipients, including diluents, preservatives, binders, lubricants, disintegrators, swelling agents, fillers, stabilizers, and combinations thereof. Liquid formulations may also contain minor amounts of polymers, surfactants, or other excipients well known to those of the art. In this context, "minor amounts" means no excipients are present that might adversely affect the delivery of assembled gel compositions to targeted tissues, e.g. through circulation.

These pharmaceutically acceptable excipients may also be included in a lyophilyzed form of the purified, self-assembled hydrogel with high agent loading content.

Formulation to Enhance Adhesion to Charged Surfaces

Generally, the hydrogel prepared, suspended, and diluted in water or an aqueous solution with a low ionic strength (or low concentration, e.g., between 0 and 500 mM) has a stronger adhesion capacity to charged surfaces than a hydrogel prepared, suspended, and diluted in phosphate buffered saline or an aqueous solution with a high ionic strength.

Dry Powder Formulations and Kit

The gelators loaded with one or more therapeutic, prophylactic, and diagnostic agents can be formulated in dry powder forms as finely divided solid formulations. The dry powder components can be stored in separate containers, or mixed at specific ratios and stored. In some embodiments, suitable aqueous and organic solvents are included in additional containers. In some embodiments, dry powder components, one or more solvents, and instructions on procedures to mix and prepare assembled nanostructures are included in a kit. Alternatively, stabilized, assembled particles, nanoparticles or bulk gel thereof are dried via vacuum-drying or freeze-drying, and suitable pharmaceutical liquid carrier can be added to rehydrate and suspend the assembled nanostructures or gel compositions upon use.

Dry powder formulations are typically prepared by blending one or more gelators, stabilizing agents, or active agents with one or more pharmaceutically acceptable carriers. Pharmaceutical carrier may include one or more dispersing agents. The pharmaceutical carrier may also include one or more pH adjusters or buffers. Suitable buffers include organic salts prepared from organic acids and bases, such as sodium citrate or sodium ascorbate. The pharmaceutical carrier may also include one or more salts, such as sodium chloride or potassium chloride. In some forms, the final carrier buffer is the same as the buffer for gel preparation and/or purification. In other forms, the final carrier buffer is not the same as the buffer for gel preparation and/or purification.

The dry powder formulations can be suspended in the liquid formulations to form suspensions of assembled particles or nanoparticles thereof, and administered systemically or regionally using methods known in the art for the delivery of liquid formulations.

Injectable Formulations

In some embodiments, the agent-loaded assembled particles are formulated for parenteral delivery, such as injection of a suspension or topical application to a mucosal surface. The formulation can be administered via any route, such as, the intravenous administration, or injected directly to the organ or tissue to be treated. For example, parenteral administration may include administration to a patient intravenously, intradermally, intraperitoneally, intravesically, intrathecally, intrapleurally, intratracheally, intramuscularly, intravaginally, subcutaneously, or subjunctivally.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection.

The carrier can be a solvent or dispersion medium containing, for example, water, buffer, ethanol, one or more polyols (e.g., glycerol, propylene glycol, and liquid polyethylene glycol), oils, such as vegetable oils (e.g., peanut oil, corn oil, sesame oil, etc.), polymers (e.g., carboxymethylcellulose, polyvinylpyrrolidone, gelatine), and combinations thereof.

The formulation is typically buffered to a pH of 4-8 for parenteral administration upon reconstitution. Suitable buffers include, but are not limited to, phosphate buffers, acetate buffers, bicarbonate, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared. For example a sterile formulation can be prepared by first performing sterile filtration of the process solutions (e.g., agent and gelator solutions), followed by gel preparation, suspension, purification and lyophilization under aseptic procession conditions. Alternatively, all processing steps can be performed under non-sterile conditions, and then terminal sterilization (e.g., gamma or E-beam irradiation) can be applied to the lyophilized hydrogel product. Sterile solution for resuspension can also be prepared using similar methods.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzyl peroxide, benzethonium chloride, benzyl alcohol, cetylpyridinium chloride, chlorobutanol, phenol, phenylethyl alcohol, and thimerosal.

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art. These preferably are enteric coated to avoid disassembly when passing through the stomach Excipients, including plasticizers, pigments, colorants, stabilizing agents, and glidants, may also be used to form coated compositions for enteral administration. Formulations may be prepared as described in standard references such as "Pharmaceutical dosage form tablets", eds. Liberman et al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules.

III. Method of Making

1. Making Nanostructured Gel Assembly with Loaded Agents

Assembled bulk gels generally contain fibrous structures from the assembly of amphiphilic gelators and drug agents. The self-assembly in the bulk gel or particles can have a variety of shapes, including micelles, vesicles, lamellae or fibers, sheets, tapes, etc.

Generally, a polar organic solvent such as DMSO, methanol, or isopropanol is used to dissolve and mix gelators and drug agents. An aqueous medium (e.g., water, hypotonic solution, isotonic solution, or hypertonic solution) is added to form a self-assembled hydrogel composition with a high agent loading.

The mixture can be heated and/or sonicated and/or placed in a bath to completely dissolve the gelator, agent and any other solid ingredients to form a homogeneous solution. The solution is then cooled under controlled conditions (e.g., temperature controlled vessel or water bath) and/or rested in an undisturbed location. The solution can transition into a viscous gel after a given time period. Gelation is deemed complete when no gravitational flow is observed upon inversion of the container at room temperature for at least 10 seconds, and in some cases, for at least 5, 10, or 15 seconds, and in some cases, for about 1, 5, 10, 30, or 60 minutes, 1 day, 2 days, 3 days, 1 week, 2 weeks, or longer. The gels preferably demonstrate stabilities of inversion of at least 60 minutes or longer. A self-assembled gel is homogeneous and stable to inversion, unlike heterogeneous materials that are a mix of gelled regions (non-flowable) and non-gelled, liquid regions (flowable).

The self-assembled gels prepared as described herein demonstrate loading efficiencies of the amine-containing agents (or other agents listed above) of up to about 90 wt/wt %, about 80 wt/wt %, about 70 wt/wt %, about 60 wt/wt %, about 50 wt/wt %, about 45 wt/wt %, about 40 wt/wt %, about 35 wt/wt %, about 30 wt/wt %, about 25 wt/wt %, about 20 wt/wt %, about 15 wt/wt %, about 10 wt/wt %, or about 5 wt/wt %.

The self-assembled gels prepared as described herein demonstrate entrapment or encapsulation efficiencies of the amine-containing agents (or other agents listed above) of up to about 100 wt/wt %, 99 wt/wt %, 98 wt/wt %, 97 wt/wt %, 96 wt/wt %, 95 wt/wt %, 94 wt/wt %, 93 wt/wt %, 92 wt/wt %, 91 wt/wt %, 90 wt/wt %, about 80 wt/wt %, about 70 wt/wt %, about 60 wt/wt %, about 50 wt/wt %, about 45 wt/wt %, about 40 wt/wt %, about 35 wt/wt %, about 30 wt/wt %, about 25 wt/wt %, about 20 wt/wt %, about 15 wt/wt %, about 10 wt/wt %, or about 5 wt/wt %.

In some instances, the gels are made with the inclusion of one or more additional salts during formation of gel, such as by adding salt(s) to an aqueous medium, such as a buffer, to tune the rheological properties of the gel, such as to impart thixotropy. For example, dissolving amphiphilic gelators in an organic solvent, such as DMSO, and adding phosphate buffered saline (PBS) containing one or more salts imparts thixotropic properties to the self-assembled gel, as compared to using water, aqueous medium, or a buffer solution without the additional salt(s) present. Exemplary salts which can be added to tune the rheological properties of the gels include, but are not limited to sodium chloride, potassium chloride, calcium chloride, magnesium chloride, zinc chloride, or combinations thereof. Any suitable salt can be used that can provide sodium, potassium, calcium, magnesium, or zinc ions. In some instances, the salt(s) are added during gel formation. In some other instances, the salt(s) are added post-gel formation, such as during a post-processing step by resuspending a formed gel in an aqueous medium containing the salt(s).

The concentration of salt(s) which can be used (added during gel formation or in post-processing) to tune the rheological properties can be in the range of between about 0.1 to about 300 mM, about 0.1 to about 300 mM, about 0.1 to about 250 mM, about 0.1 to about 200 mM, about 0.1 to about 150 mM, about 0.1 to about 100 mM, about 0.1 to about 50 mM, or about 0.1 to about 25 mM, as present in an aqueous medium (used in preparation of the gel or to resuspend a formed gel) or present as the concentration in the final gel including the salt(s).

In some instances, the salt(s) described here are added to buffer(s), such as a phosphate buffer, used to prepare the gels or in which a prepared gel may be resuspended in at concentrations ranging from between about 1 to 250 mM, about 1 to 200 mM, about 1 to 150 mM, about 1 to 100 mM, about 1 to 75 mM, about 1 to 50 mM, or about 1 to 25 mM. In some other instances, the salt(s) described here are added to buffer(s), such as a phosphate buffer, used to prepare the gels or in which a prepared gel may be resuspended in at concentrations of about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150 mM, or higher. The concentration of the one or more salts in the final gels after all processing steps may be at concentrations of about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150 mM, or higher.

In some instances, the gels are made with the inclusion of one or more organic solvents either during formation of gel or added post-gel formation, such as during a post-processing step in order to tune the rheological properties of the gel, such as to impart thixotropy. Exemplary organic solvents which can be used, either alone or in combination with the salt(s) already discussed, to tune the rheological properties of the gels include, but are not limited to dimethylsulfoxide (DMSO), alcohols (such as methanol, ethanol, isopropanol, t-butanol). In some other instances, the organic solvent(s) described here are added as part of gel formation or can be added to buffer(s), such as a phosphate buffer, in which a prepared gel may be resuspended to provide gels with concentrations of organic solvent(s) of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, or 25% (volume/volume of total gel).

In yet other instances, the gels are made to include the addition of a combination of salt(s) and organic solvent(s), as described immediately above, in order to tune the rheological properties of the gel, such as to impart thixotropy. In such instances where the rheological properties are tuned, such as to impart thixotropic properties to the gel, the amounts of salt(s) and/or organic solvent(s) used in preparing the gel can be selected or controlled to preferably obtain encapsulation efficiencies of the amine-containing agent (or other agents above) to be at least about 50 wt/wt %, about 45 wt/wt %, about 40 wt/wt %, about 35 wt/wt %, about 30 wt/wt %, about 25 wt/wt %, about 20 wt/wt %, about 15 wt/wt %, about 10 wt/wt %, or about 5 wt/wt % in the gel.

In some instances, the gels can be formed without any additional salts and/or organic solvents or their rheological properties can be tuned by addition of salts and/or organic solvent(s) (either during gel formation or post-gel formation). The gels described can have or can be tuned to have a storage modulus (G') of from about 0.1, from about 0.2, from about 0.3, from about 0.4, from about 0.5, from about 0.6, from about 0.7, from about 0.8, from about 0.9, from about 1, from about 2, from about 3, from about 4, or from about 5 Pascals up to about 50, about 75, about 100, about 150, about 200, about 250, or about 300, or any combination of upper and lower end points disclosed herein. The gels described can have or can be tuned to have a loss modulus (G") of from about 0.1, from about 0.2, from about 0.3, from about 0.4, from about 0.5, from about 0.6, from about 0.7, from about 0.8, from about 0.9, from about 1, from about 2, from about 3, from about 4, or from about 5 Pascals up to about 10, about 15, about 20, about 25, about 30, about 35, about 40, or about 300 Pascals, or any combination of upper and lower end points disclosed herein.

In some instances, the gels are made with or without addition of salts and/or organic solvent(s) (either during gel formation or post-gel formation) and have viscosities in a range from between about 0.1, from about 0.2, from about 0.3, from about 0.4, from about 0.5, from about 0.6, from about 0.7, from about 0.8, from about 0.9, from about 1, from about 2, from about 3, from about 4, or from about 5 centipoise (cP) up to about 10, about 100, about 200, about 300, about 400, about 500, about 600, about 700, about 800, about 900, about 1,000, about 1,100, about 1,200, about 1,300, about 1,400, about 1,500, about 1,600, about 1,700, about 1,800, about 1,900, about 2,000, about 2,500, or about 3000 cP, or any combination of upper and lower end points disclosed herein. In some instances, the gels formed addition of salts and/or organic solvent(s) (either during gel formation or post-gel formation) exhibit thixotropic properties such that the viscosity of the gel changes (i.e., decreases) upon exposure to shear, for example, but returns to its original viscosity or returns substantially back to its original viscosity.

Distillation, filtration, dialysis and centrifugation techniques may be used to remove unencapsulated excess agent and undesired solvent from the gels. In some embodiments, purification using pure water or low ionic strength solutions are preferred over high ionic strength solutions to improve retention of loaded agent. In some embodiments, water or other aqueous medium with a low ionic strength represented by a salt concentration below 0.15 M as the dialysis medium maintains a higher level of agent loading in hydrogel compared to saline solution with 0.15 M salt or higher.

When the stabilized, self-assembled gel compositions do not include a solvent, a gelator can be combined with a liquid amphiphile such as a vitamin-derived liquid amphiphile to form a mixture entrapping drug agents. The mixture can include one or more gelators, one or more stabilizing agents, and one or more liquid amphiphiles. The mixture is then heated/sonicated/placed in a bath to form a homogenous solution. The resulting solution is then allowed to cool and/or rest in an undisturbed location. The solution can transition into a viscous gel after a given time period.

In some embodiments, one or more gelators and optionally an agent to be encapsulated can be combined in the absence of a solvent to form a mixture. The mixture is then heated/sonicated/placed in a bath to form a homogenous solution. The resulting solution is then allowed to cool and/or rest in an undisturbed location. The solution can transition into a viscous gel after a given time period.

In some embodiments, a melted gel including one or more gelator and one or more solvents can be added to a solid agent, to an agent dissolved in the same one or more solvents, or to an agent dissolved or suspended in a gel-compatible solvent, in order to encapsulate the agent.

In some embodiments, the gel is heated to temperatures between 40 to 110° C., depending on the temperature sensitivity of the gelators, stabilizing agents, solvent/buffer content, and/or active agents. These mixtures can be heated and/or sonicated and/or placed in a bath for a duration of from one to 30 minutes or longer until all material is dissolved. The solutions are cooled to a temperature of from −20 to 37° C. and/or rested for a duration of from 15 minutes, 30 minutes, 45 minutes to an hour, hours, one, two or three days.

Nanostructures are formed in the solidified gels. In some embodiments, the nanostructures can be fibers, sheets or particles with a length and/or width of one micron, two microns, three microns, four microns, five microns, ten microns, twenty microns, or twenty five microns. The nanostructures can aggregate into networks, and/or be in the form of a liquid crystal, emulsion, fibrillar structure, or tape-like morphologies. When the nanostructures are in the form of fibers, the fibers can have a diameter of about 2 nm or more, and can have lengths of hundreds of nanometers or more. In some embodiments, the fibers can have lengths of one micron, two microns, three microns, four microns, five microns, ten microns, twenty microns, or twenty-five microns or more.

When amphiphilic molecules self-assemble in a solvent, hydrophobic and hydrophilic portions of the gelator molecules can interact to form lamellae of gelator molecules. In some embodiments, when the gels are hydrogels, the hydrophobic portions of gelators are located in the inner regions of a given lamella, and hydrophilic portions are located at the outer surfaces of the lamella. In some embodiments, when the gels are organo-gels, the hydrophobic portions of gelators are located in the outer regions of a given lamella, and hydrophilic portions are located at the inner surfaces of the lamella. The lamella can have a width of from about three to about five nanometers and a length of several microns. Several tens or hundreds of such lamellae can bundle together to form nanostructures, such as fibers of nano-sized width (e.g. 100-900 nm with lengths of several microns or longer) and sheet-like structures.

The gelators can be at least 10 mole %, 20 mole %, 30 mole %, 40 mole %, 50 mole %, 60 mole %, 70 mole %, 80 mole %, or 90 mole % of the total amount of hydrogel composition excluding solvent (e.g., gelators, therapeutically active agents, and optional stabilizing agent). The gelators are dissolved in the solvent to between 0.01 and 50 wt % (e.g., up to 500 mg/mL).

2. Suspension into Fibrous Mixture and Processing into Particles

In some embodiments, the self-assembled gel is suspended in a low ionic strength aqueous solution (e.g., by homogenization) and is isolated through repeated cycles of centrifugation (e.g., 2,000-25,000 rpm for 2-15 minutes) and resuspension/washing to provide water dispersible self-assembled nanostructures from pelleted gel. In some forms, the bulk gel is suspended in water and/or phosphate buffered saline ("PBS") and homogenized or sonicated to break up the bulk gel into particles which retain the fibrous nanostructures formed in the bulk gel.

In some embodiments, the self-assembled gel is suspended in a low ionic strength aqueous solution (e.g., by homogenization) and is isolated through dialysis or tangential flow filtration to provide water dispersible self-assembled nanostructures from pelleted gel.

In some embodiments, the nanostructures can have a minimum dimension (e.g., a thickness, a width, or a diameter) of 2 nm or more up to 500 nm when measured in a dry environment such as the vacuum dried sample in scanning electron microscopy; or a minimum dimension of 10 nm, 50 nm, 100 nm, 200 nm, 300 nm, 400 nm, 500 nm or more when measured for hydrodynamic sizes via dynamic light scattering. The nanoparticles can have a hydrodynamic diameter between 100 nm and 990 nm, preferably between 500 nm and 900 nm, and the nanoparticles maintain at least 50, 60, 70 or 80% of the size in serum over a period of at least two hours.

IV. Methods of Use

The formulation can be administered via a variety of routes such as injection directly to the organ or tissue to be treated, placement at the time of surgery, topical application to a wound, or placement on a mucosal surface in the nasal cavities, eye, oral or buccal surfaces, vaginally or rectally. For example, parenteral administration may include administration intravenously, intradermally, intraperitoneally, intravesically, intrathecally, intrapleurally, intratracheally, intramuscularly, intravaginally, subcutaneously or subjunctivally.

The agent-loaded gel compositions can be administered through various known regional delivery techniques, including injection, instillation using catheters, implantation, inhalation using aerosols, and topical application to the mucosa, such as the oral or buccal surfaces, nasal or pulmonary tracts, intestinal tracts (orally or rectally), vagina, or skin. In situ self-assembly of stabilized nanostructures allows for regional delivery of the compositions and stimuli-responsive delivery of active agents. When esterases are present or inflamed tissues release enzymes, the enzyme disassembles gel compositions, which releases amine-containing agents such as lidocaine or other such compounds, and any other agents, such as described herein. After the agent(s) is released, the enzyme concentration decreases. The gel compositions that are not cleaved remain stable, until another inflammatory stimulus for "on-demand release", where the pathological environment regulates the amount and timing of an agent release. In some embodiments, the compositions can be used to release therapeutic agents that correlate with different stages of tissue regeneration.

The gel may be administered in hydrated form or dried. It may be provided in a kit in a sterile lyophilized package, optionally with rehydration media. It may be attached to an adhesive bandage, such as a bandaid in place of the standard absorbent pad.

It may be resuspended at the time of use, or provided in solid form which is cut into a size to deliver a desired dose, then administered dried or rehydrated.

In the preferred embodiments, the agents are local anesthetics, antiinfectives such as antibiotics, antimicrobials, and/or anti-inflammatories. The formulation is applied to the site where pain relief, treatment of infection, or killing of cells is desired, or to a site adjacent thereto.

In some embodiments, the gel compositions can be controllably disassembled, for example, upon exposure to hydrolytic or enzymatic degradation, or by exposure to an external stimulus. Gels can be disassembled by cleavage of a labile linkage in an amphiphilic gelator, such as an ester, amide, anhydride, carbamate, phosphate-based linkages (e.g., phosphodiester), disulfide (—S—S—), acid-cleavable groups such as —OC(O)—, —C(O)O—, or —C=NN— that can be present between a hydrophobic and hydrophilic group within the gelator. Examples of labile linkages are also described, for example, in PCT publication WO2010/033726.

In some embodiments, encapsulated agents is controllably released from the gel compositions upon gel disassembly. For example, encapsulated agents can be gradually released over a period of time (e.g., a day, a week, a month, six months, or a year). Depending on the parameters, release can be delayed or extended from minutes to days to months, for example, when gel compositions are administered under physiological conditions (a pH of about 7.4 and a temperature of about 37° C.).

Different parameters can be used to control release. For example, sustained release can be controlled by the concentration of an enzyme and/or a temperature. Release can be accelerated using a high enzyme concentration, for example, by delivery to an area of infection, characterized by elevated enzyme concentrations, or low pH, for example, in tumors or areas of infection. In some embodiments, the sustained release occurs without a burst release, or with only a minimal burst release.

In some embodiments, the agent-loaded assembled gel compositions or nanofibrous particles are used to deliver one or more local anesthetics into inflamed tissue to treat one or more symptoms of inflammation. In other embodiments, the agent-loaded assembled gel compositions or nanofibrous particles are used to deliver one or more active agents into the tumor tissues for sustained delivery of the agents and even uptake by tumor cells which produce esterases, and inflamed tissues release enzymes, both of which provide pathology-specific degradation of pro-drug gelators and release of active agents. Compared with active agents delivered in its free forms, the agent-loaded assembled compositions partition in inflamed and/or tumor tissues, i.e., accumulate in inflamed and/or tumor tissues more than in non-inflamed or non-tumor tissues.

Alternatively, the gelators with drug agents can be applied to a biological system and self-assembly can occur in situ. For example, the gel compositions described herein may be applied to the surface of bone and the gel can be assembled within the pores of the bone. For example, heated gel compositions can be injected in solution form to a bone site, which can then cool to physiological temperatures to assemble into gel forms.

The agent-loaded gel compositions or nanofibrous particles can be useful for improving targeting efficiency, efficacy, safety, and compliance benefiting from single dose, prolonged action or tissue-specific formulations, compared to delivery of active agents in its free form or delivery from a co-solvent assisted gel composition.

Exemplary diseases or disorders to be treated with the agent-loaded gel composition include, but are not limited to, allergy (e.g. contact dermatitis), arthritis, asthma, cancer, cardiovascular disease, diabetic ulcers, eczema, infections, inflammation, mucositis, periodontal disease, psoriasis, respiratory pathway diseases (e.g., tuberculosis), vascular occlusion, pain, graft versus host diseases, canker sores, interstitial cystitis, Hunner's lesions, post-operative pain, peripheral neuropathy, bacterial conditions, viral conditions.

The present invention will be further understood by reference to the following non-limiting examples.

EXAMPLES

Example 1: Use of Aqueous Salt Solutions as the Medium for Gel Formation Increases Loading of Lidocaine; Use of Water as the Suspension Medium Maintains High Loading of Lidocaine Materials & Methods
Preparation of Hydrogel in DMSO-Water System:

A stock solution (20.4 wt/wt %) of ascorbyl palmitate (AP) in DMSO was prepared by dissolving 3.95 grams of ascorbyl palmitate in 15.23 grams of DMSO. The stock solution (2.0 g) was dispensed into two 20 mL scintillation vials containing lidocaine free base as a white solid. The first vial contained 120 mg lidocaine and the second contained 60 mg lidocaine. Pure HPLC grade water (5.6 mL) was added to each vial and the resulting suspensions were heated in a hot water bath at 80° C. for 6 minutes with stirring. The vials were removed from the hot water bath and cooled in a room temperature water bath for 30 minutes (theoretical lidocaine loading of 13% and 23%, for the 120 mg and 60 mg preparations, respectively). The vials were then removed from the water bath and left undisturbed at room temperature for an additional 2 hours. The resulting hydrogels were suspended in water (8 mL) to achieve a final volume of 15 mL.

Drug loading was calculated as relative to the solid content only. The addition of 2 grams of the stock solution containing AP in DMSO resulted in a gel containing 0.41 grams of AP. Therefore, the theoretical lidocaine loading of the sample containing 120 mg lidocaine, which used 2 g of the AP/DMSO stock solution, is calculated as follows:

Loading=0.12 grams/(0.12+0.41 grams)=23%.

Preparation of Hydrogel in DMSO-PBS System:

A stock solution (20.4 wt/wt %) of ascorbyl palmitate in DMSO was prepared by dissolving 3.95 grams of ascorbyl palmitate in 15.23 grams of DMSO. The stock solution (2.0 g) was dispensed into a first 20 mL scintillation vial containing lidocaine free base (120 mg) as a white solid. In a second vial, ascorbyl palmitate (200 mg) and lidocaine free base (30 mg) were dissolved in DMSO (0.7 mL). Phosphate buffered saline was added to the vials (5.6 mL to the first vial, and 2.8 mL to the second vial) and the resulting suspensions were heated in a hot water bath at 80° C. for 6 minutes with stirring. The vials were removed from the hot water bath and cooled in a room temperature water bath for 30 minutes. The vials were then removed from the water bath and left undisturbed at room temperature for an additional 2 hours.

The resulting hydrogels were suspended in water (8 mL) to achieve a final volume of 15 mL.

To study the impact of suspension medium, PBS (8 mL) was also used instead of water to suspend the hydrogel formed in the DMSO-PBS system to a final volume of 15 mL.

Assessment of Loading and Encapsulation Efficiency:

Aliquots of suspended hydrogel (1 mL) were transferred to centrifuge tubes and centrifuged at 14,000 RCF for 8 minutes. The supernatant was removed by pipette and diluted 1:100 in pure water. The residual pellet was dissolved in DMSO (1 mL) and diluted 1:100 in 1% citric acid in methanol. The lidocaine and ascorbyl palmitate content in the supernatant and residual pellet was assayed by HPLC to assess encapsulated lidocaine and free (i.e., unencapsulated) lidocaine content of the formulation.

Results

The amounts of loaded lidocaine in the formed ascorbyl palmitate hydrogels formed in water and PBS were quantified and shown in Table 1.

TABLE 1

Effects of PBS and water on lidocaine loading in ascorbyl palmitate hydrogels during gel formation.

| Formulation | Theoretical Loading (mg Lidocaine/ mg total) | Actual Loading (mg Lidocaine/ mg total) | % Encapsulated/ % Free |
|---|---|---|---|
| Lidocaine: AP - PBS | 23% | 10.7% | 43%/57% |
| Lidocaine: AP - PBS | 13% | 4.2% | 38%/62% |
| Lidocaine: AP - H$_2$O | 23% | 0.3% | 1.6%/98.4% |
| Lidocaine: AP - H$_2$O | 13% | 0.0% | 0.3%/99.7% |

An aqueous salt solution, here phosphate buffered saline (PBS), as the aqueous component during gel formation significantly increased the loading of lidocaine compared to a gel formed using water.

Hydrophilic small molecule, lidocaine, is generally not efficiently encapsulated in an ascorbyl palmitate hydrogel formed in a co-solvent system of pure water and DMSO. The necessity of using salt in the gel preparation step can be due to a number of factors, which may be related to electrostatic interactions, gel swelling/collapsing, or other mechanisms, alone or in combination, which associate or entrap lidocaine in the gel.

Although PBS was preferred over water in permitting a high loading of lidocaine in the gels as shown in Table 1, water as the suspension medium was superior to PBS in maintaining the higher loading (Table 2).

TABLE 2

Effects of PBS and water on lidocaine loading in ascorbyl palmitate hydrogels during gel suspension

| Formulation Lidocaine: AP PBS | Actual Loading (mg Lidocaine/ mg total) | % Encapsulated |
|---|---|---|
| PBS | 7.9 ± 0.3% | 31.6 ± 1.3% |
| Water | 9.3 ± 1.2% | 36.3 ± 5.9% |
| p value | <0.05 | 0.12 |

Example 2: Purification in a Salt-Free Medium Greatly Reduces Leakage of Lidocaine from Hydrogels Compared to Salt-Containing Solutions Materials & Methods Centrifugation:

To remove impurities such as excess drug and solvent (e.g., DMSO), suspended hydrogels were centrifuged and the supernatant containing any soluble impurities, such as excess drug and DMSO, was discarded. The gel pellet was resuspended in PBS or water. The centrifugation and resuspension process was repeated at least three times for gel purification.

Dialysis:

Dialysis was performed using an 8-10 kDa molecular weight cutoff dialysis bag, water or PBS as the external phase in an ~1000 fold volume excess relative to the sample volume, and performing 3-5 water or PBS changes over the course of 2 days.

Results

Repeated centrifugation and resuspension in PBS disrupted the gel and caused a portion of lidocaine to be released with each wash cycle (FIG. 1). Therefore, centrifugation as the purification technique using PBS to remove excess solvent and free drug was therefore ineffective for purifying hydrogel containing a hydrophilic drug while maintaining the drug loading. FIG. 1 shows centrifugation cycles in PBS rapidly decreased the loading of lidocaine from an ascorbyl palmitate hydrogel prepared by first dissolution in PBS and containing 13% lidocaine (denoted AP:lidocaine-PBS 13%). High loading levels could be preserved when using pure water as the washing/resuspension solution for centrifugation. Three centrifugation cycles with resuspension in water preserved 92% of the loading and increased the % encapsulation to 91%. In contrast, using PBS for three wash cycles preserved only 20% of the drug loading and only increased the % encapsulated to 53% (FIG. 1).

In dialysis, the hydrogel fibers were effectively retained inside of the dialysis tubing because their dimensions were much larger than the pore openings of the tubing. As shown in Table 3, the % free drug was significantly reduced using dialysis with water as the external phase, with only a small decrease in the gel loading. These results are consistent with centrifugation in that water as the purification medium can preserve drug loading while increasing the % encapsulated (i.e., removing excess free drug). Dialysis performed using PBS in place of water caused a complete loss of drug loading, similar to centrifugation with PBS as the suspension phase. These data suggest that pure water is effective at retaining high drug loadings during liquid-based purification methods, whereas the presence of salt causes gel disruption and loss of drug loading.

The presence of salt is necessary during the gel formation step to achieve high drug loadings (Table 1); whereas in purification, a salt-free medium minimizes the leakage of encapsulated agent from gel.

TABLE 3

Effects of dialysis on Lidocaine encapsulation and loading levels.

| Formulation Lidocaine: AP PBS | Actual Loading (mg Lidocaine/ mg total) | % Encapsulated/ % Free |
|---|---|---|
| Before Dialysis | 7.9% | 32%/68% |
| After Dialysis | 6.6% | 96%/4% |

This finding provided a means for controlling two important aspects of the formulation: (1) free vs. encapsulated content (since free drug can be added back to a purified formulation to a desired level), and (2) the composition of the suspension fluid, which is important for formulation stability, lyophilization/resuspension, and gel adhesion to tissues and other surfaces.

Example 3: Preparation, Suspension, and Dilution in Water Improves the Adhesion Level of Ascorbyl Palmitate Hydrogel to Charged Surfaces Compared with Preparation, Suspension, and Dilution in PBS Materials & Methods Ascorbyl palmitate (AP, 20-25 mg) was added to a glass vial and then dissolved in DMSO (3.5 µL per mg AP). Water or PBS was then added (4 mL per mL DMSO) and the mixture was heated using a heat gun for 50 seconds. Vials were then placed undisturbed on the benchtop for 30 minutes. At this point, 1 mL of water or PBS was added to the water or PBS gels, respectively, and the gels were suspended by vigorous agitation. Gels were then diluted into 9 mL of water or PBS, respectively. Each solution (1 mL) was added to one well of a 24-well amine-coated polystyrene plate and left undisturbed for 30 minutes. At this point, the gels suspensions were removed with a pipette and the wells were washed with water or PBS, respectively (1 mL per wash with brief agitation, six times in total). The wells were then imaged using an iRiS Digital Imaging System (Logos Biosystems) at 10× magnification. After imaging, 0.5 mL ethanol was added to each well for 2 minutes to dissolve the AP gel particles that adhered to the surface. Two hundred microliters of each solution was then transferred to a UV-transparent 96-well plate and the absorbance was measured at 254 nm. The AP content of the solution was quantified using a calibration curve of AP prepared in ethanol. The mass of AP measured in each sample was then normalized by the well area of the polystyrene plate.

Results

Digital imaging confirmed more attachment of AP gel on amine-coated polystyrene plates when the gel was prepared, suspended, and diluted in water than the gel prepared, suspended, and diluted in PBS. For the AP gel prepared, suspended and diluted in water, the adhesion level was 17 µg/cm². In comparison, the AP gel prepared, suspended and diluted in PBS had an adhesion level of 2 µg/cm². This result demonstrates that lower ionic strength (water rather than PBS) lead to significant increases in AP gel adhesion to positively charged surfaces by over 8-fold.

Example 4: Preparation of Gels Using Different Solvents and Reduced Aqueous Content Improves Lidocaine Loading and Percent Encapsulated Materials & Methods Hydrogels were prepared as described for the first vial in example 1, Preparation of Hydrogel in DMSO-PBS System.

Six variations were made in this experiment: (1) for one preparation, the PBS level was reduced from 5.6 mL to 2.8 mL (i.e., changing from a 4:1 to a 2:1 PBS:DMSO ratio), (2) for a second gel preparation, the PBS level was reduced from 5.6 mL to 1.4 mL (i.e., changing from a 4:1 to a 1:1 PBS:DMSO ratio), and (3) for the remaining gel preparations, the solvent was methanol, ethanol, isopropanol, or t-butanol and water was used at 2.8 mL (i.e., 2:1 $H_2O$:methanol; 2:1 $H_2O$:ethanol; 2:1 $H_2O$:isopropanol; 2:1 $H_2O$:t-butanol). Hydrogels were suspended in water, as described above, and assayed for gel loading and percent encapsulated.

Results

Hydrogel loading and percent encapsulated results are presented in Table 4. Reducing the aqueous content improves lidocaine loading and percent encapsulated in the DMSO system. Switching from DMSO to methanol results in almost 100% drug encapsulation and loading that is 98% of the theoretical. We also tested the effect of other alcohols instead of methanol with increases in reductions of drug encapsulation percentage and loading as the solvent was switched from methanol to ethanol, isopropanol, or t-butanol, as detailed in Table 4. These results demonstrate the importance of solvent type and the relative ratio of organic-to-aqueous volumes on gel loading and percent encapsulated.

TABLE 4

Effect of aqueous volume and solvent type on lidocaine loading and percent encapsulated.

| Formulation | Actual Loading (mg Lidocaine/ mg total) | % Encapsulated/ % Free | Gelation Result |
|---|---|---|---|
| Lidocaine: AP - PBS:DMSO 4:1 | 10.7% | 43%/57% | invertible gel |
| Lidocaine: AP - PBS:DMSO 2:1 | 12.2% | 46%/54% | invertible gel |
| Lidocaine: AP - PBS: DMSO 1:1 | 17.5% | 67%/33% | invertible gel |
| Lidocaine: AP - $H_2O$:methanol 2:1 | 22.6% | 96%/4% | invertible gel |
| Lidocaine: AP - $H_2O$:ethanol 2:1 | 21.3% | 91%/9% | invertible gel |

TABLE 4-continued

Effect of aqueous volume and solvent type on lidocaine loading and percent encapsulated.

| Formulation | Actual Loading (mg Lidocaine/ mg total) | % Encapsulated/ % Free | Gelation Result |
|---|---|---|---|
| Lidocaine: AP - H$_2$O:isopropanol 2:1 | 19.1% | 78%/22% | non-invertible gel |
| Lidocaine: AP - H$_2$O:t-butanol 2:1 | 17.8% | 74%/26% | non-invertible gel |

Example 5: The Use of Salt to Control Formulation Loading

Materials & Methods

Preparation of Hydrogel in Methanol-Phosphate Buffer (PB) pH 7.4 with Added NaCl:

A stock solution (20.4 wt/wt %) of ascorbyl palmitate (AP) in methanol was prepared by dissolving 3.95 grams of ascorbyl palmitate in 15.43 grams of methanol. The stock solution (2.0 g) was dispensed into five 20 mL scintillation vials, each containing 120 mg lidocaine free base as a white solid. Phosphate buffer (PB) pH 7.4 containing 0, 50, 100, 150 or 300 mM NaCl was added to each vial at 2.8 mL and the resulting suspensions were heated in a hot water bath at 80° C. for 6 minutes with stirring. The vials were removed from the hot water bath and cooled in a room temperature water bath for 30 minutes (theoretical lidocaine loading of 23%). The vials were then removed from the water bath and left undisturbed at room temperature overnight. The resulting hydrogels were suspended in water (8 mL) to achieve a final volume of 15 mL.

Preparation of Hydrogel in Methanol-Phosphate Buffer (PB) pH 7.4 with NaCl Added after Gel Purification:

A stock solution (20.4 wt/wt %) of ascorbyl palmitate (AP) in methanol was prepared by dissolving 3.95 grams of ascorbyl palmitate in 15.43 grams of methanol. The stock solution (2.0 g) was dispensed into five 20 mL scintillation vials, each containing 120 mg lidocaine free base as a white solid. Phosphate buffer (PB) pH 7.4 was added to each vial at 2.8 mL and the resulting suspensions were heated in a hot water bath at 80° C. for 6 minutes with stirring. The vials were removed from the hot water bath and cooled in a room temperature water bath for 30 minutes (theoretical lidocaine loading of 23%). The vials were then removed from the water bath and left undisturbed at room temperature overnight. The resulting hydrogels were suspended in water (8 mL) to achieve a final volume of 15 mL.

To remove impurities such as excess drug and solvent (e.g., methanol), suspended hydrogels were centrifuged and the supernatant containing any soluble impurities, such as excess drug and methanol, was discarded. The gel pellet was resuspended in water. The centrifugation and resuspension process was repeated at least three times for gel purification. After the final centrifugation step, the pellet was resuspended in 15 mL of PB containing 0, 50, 100, 150, or 300 mM NaCl.

Preparation of Hydrogel in Methanol-Phosphate Buffer (PB) pH 7.4 with Added NaCl, KCl, CaCl$_2$, MgCl$_2$, or ZnCl:

A stock solution of (20.4 wt/wt %) ascorbyl palmitate in methanol was prepared by weighing 4.3955 grams of ascorbyl palmitate in 16.9227 grams of DMSO. The stock solution (2.0 g) was dispensed into ten 20 mL scintillation vials, each containing 120 mg lidocaine free base as a white solid. Phosphate buffer (10 mM, pH 7.4) containing NaCl, KCl, CaCl$_2$, MgCl$_2$, or ZnCl was prepared at two concentrations (50 or 150 mM). The PB buffers containing the aforementioned salts were added to the scintillation vials and the resulting suspensions were heated at 80° C. for 6 minutes with stirring. The vials were removed from the hot water bath and left undisturbed at room temperature overnight. The resulting hydrogels were suspended in water (8 mL) to achieve a final volume of 15 mL.

Results

Hydrogel loading and percent encapsulated results are presented in Table 5 below for methanol-phosphate buffer pH 7.4 with added NaCl either during gel preparation or during gel purification. In the methanol-based hydrogel system, the addition of salt to the aqueous phase can be used to control the level of free vs. encapsulated lidocaine, and therefore, the gel loading level. This salt effect can be used both in the gel preparation and purification steps, and is dose dependent (i.e., the reduction in the loading or in the encapsulation % increases as the amounted of added salt increases).

TABLE 5

Effects of salt on loading and % encapsulated in the methanol-PB system.

| Salt added | PB:methanol 2:1 system with salt added | | | |
|---|---|---|---|---|
| (final concentration mM) | During gel preparation | | During gel purification | |
| | Loading | % Encapsulated | Loading | % Encapsulated |
| 0 | 22.3% | 93.1% | 19.6% | 83.8% |
| 50 | 17.8% | 71.6% | 10.9% | 42.0% |
| 100 | 15.0% | 56.5% | 7.7% | 27.7% |
| 150 | 11.0% | 40.1% | 6.8% | 25.4% |
| 300 | 9.1% | 35.3% | 4.6% | 16.0% |

Hydrogel loading and percent encapsulated results are presented in Table 6 below for methanol-phosphate buffer pH 7.4 with NaCl, KCl, CaCl$_2$, MgCl$_2$, or ZnCl added during gel preparation. Increasing salt concentration in the PB formulation buffer decreases lidocaine loading for NaCl, KCl, CaCl$_2$, MgCl$_2$, and ZnCl. The relative changes in loading and encapsulation were comparable across all tested chloride salts, however differences were observed in the resulting gel's bulk properties. These differences may be caused by the counter cations (Na$^+$, K$^+$, Ca$^{2+}$, Mg$^{2+}$, Zn$^+$) affecting the higher-order self-assembly of ascorbyl palmitate hydrogels.

TABLE 6

Effects of chloride salts on loading and % encapsulated in the DMSO-PB system.

| Salt added during gel preparation | Salt concentration of formulation buffer (mM) | Actual Loading (mg Lidocaine mg total) | % Encapsulated/ % Free | Gelation Result |
|---|---|---|---|---|
| NaCl | 50 | 12.4 | 47%/53% | invertible gel |
| NaCl | 150 | 7.6 | 25%/75% | invertible gel |
| KCl | 50 | 11.1 | 40%/60% | invertible gel |
| KCl | 150 | 6.9 | 25%/75% | viscous soft gel |

TABLE 6-continued

Effects of chloride salts on loading and % encapsulated in the DMSO-PB system.

| Salt added during gel preparation | Salt concentration of formulation buffer (mM) | Actual Loading (mg Lidocaine mg total) | % Encapsulated/ % Free | Gelation Result |
|---|---|---|---|---|
| CaCl$_2$ | 50 | 8.6 | 30%/70% | precipitated |
| CaCl$_2$ | 150 | 0.3 | 1%/99% | precipitated |
| MgCl$_2$ | 50 | 13.0 | 32%/68% | dense invertible gel |
| MgCl$_2$ | 150 | 9.8 | 29%/71% | dense invertible gel |
| ZnCl | 50 | 7.3 | 26%/74% | invertible gel |
| ZnCl | 150 | 3.2 | 11%/89% | viscous soft gel |

Example 6. Effects of NaCl and DMSO on Hydrogel Rheological Properties

Materials and Methods

Preparation of Hydrogel 1: Hydrogel prepared as described for the first vial in Example 1.

Preparation of Hydrogel 2: Hydrogel prepared as described for the first vial in Example 1. After resuspending to a volume of 15 mL, the hydrogel suspension was diluted with water to a final volume of 35 mL. The suspension was centrifuged for 10 minutes at 4° C. at 5,000 RPM. The supernatant was decanted and the residual solid was resuspended to 35 mL in water, centrifuged again. This process was repeated for 3 total centrifuge cycles. After the third centrifuge cycle, the residual solid sample was resuspended in water (3.2 mL) and a lidocaine stock solution (6.8 mL) containing lidocaine HCl.H$_2$O (157 mM), and sodium bicarbonate (32 mM).

Preparation of Hydrogel 3: Ascorbyl palmitate (400 mg) and lidocaine (120 mg) were weighed into a 20 mL scintillation vial and dissolved in methanol (1.4 mL). Water (2.8 mL) was added to the solution and the resulting suspension was heated in a water bath at 80° C. for 6 minutes with stirring. The vial was removed from the hot water and placed a room temperature water bath overnight. The hydrogel was resuspended in water (15 mL), transferred to a conical centrifuge tube, and diluted to a final volume of 35 mL. The suspensions were centrifuged for 10 minutes at 4° C. at 5,000 RPM. The supernatant was decanted and the residual solid was resuspended to 35 mL in water, centrifuged again. This process was repeated for 3 total centrifuge cycles. After the third centrifugation cycle, the residual solid was resuspended in water (1 mL) and a pH 6.59 stock solution (6.4 mL) containing NaCl (300 mM) and sodium phosphate (10 mM).

Preparation of Hydrogel 4: Hydrogel was prepared through the centrifugation process as Hydrogel 3 in Example 6. After the third centrifuge cycle, the residual solid samples were resuspended in water (1.5 mL) and a pH 6.98 stock solution (6.75 mL) containing NaCl (130 mM), sodium phosphate (8.1 mM) and DMSO (18.7%; vol/vol).

Preparation of Hydrogel 5: Hydrogel was prepared through the centrifugation process as Hydrogel 3 in Example 6. After the third centrifugation, the residual solvent was resuspended in a stock solution (6.4 mL) containing NaCl (50 mM).

Results

Hydrogel formulation characteristics are listed in Table 7. The pH and final concentrations of ascorbyl palmitate and lidocaine are intended to be identical or similar for each formulation. The amount of NaCl and DMSO is varied to demonstrate their effect on hydrogel rheology.

TABLE 7

Formulation characteristics for Hydrogels 1-5.

| | Ascorbyl Palmitate (mg/mL) | Lidocaine (mg/mL) | NaCl (mM) | % DMSO (vol/vol) | % Loading | % Encapsulated | pH |
|---|---|---|---|---|---|---|---|
| Hydrogel 1 | 27.8 | 8.5 | 52 | 9.3 | 7.6 | 26.8 | 6.39 |
| Hydrogel 2 | 26.2 | 8.1 | 0 | 0 | 13.6 | 33.0 | 6.66 |
| Hydrogel 3 | 26.1 | 8.0 | 150 | 0 | 8.4 | 32.5 | 6.32 |
| Hydrogel 4 | 26.1 | 7.5 | 65 | 9.3 | 7.5 | 39.9 | 6.26 |
| Hydrogel 5 | 26.8 | 8.1 | 25 | 0 | 17.0 | 67.5 | 5.97 |

Each of the 5 hydrogel samples were analyzed on a TA Instruments AR-G2 rheometer. The time sweep, shear sweep, and thixotropy for each formulation is listed in Table 8 and FIGS. 2A-2E show the storage modulus G', loss modulus G", and phase angle of the hydrogels. Hydrogel 1 results in the strongest gel (highest G', G"), with highest yield stress and equilibrium viscosity. Hydrogel 2, with no salt or DMSO, is the weakest gel with very low viscosity. Hydrogel 3, with salt and no DMSO, is weaker and less viscous than hydrogel 1. Hydrogel 4 contains DMSO and NaCl that are added post processing which results in decreased G' and G" as well as lower viscosity compared to hydrogel 1. Finally, hydrogel 5, with low levels of salt and no DMSO is stronger than hydrogel 2 but weaker than hydrogels 1, 3 and 4.

TABLE 8

Dynamic moduli at the end of time sweep step, yield stress in a shear rate sweep step, and viscosity at the start and end of a constant shear rate step.

| | Time Sweep (60 minutes) | | | | Shear sweep | Thixotropy (30 minutes) | |
|---|---|---|---|---|---|---|---|
| | G' [Pa] | G" [Pa] | G* [Pa] | Delta [degrees] | Yield Stress [Pa] | Viscosity [Pa · s] Start | End |
| Hydrogel 1 | 204.40 | 19.37 | 205.30 | 5.4 | 44.04 | 0.04 | 1.92 |
| Hydrogel 2 | 0.05 | 0.08 | 0.10 | 58.6 | 0.01 | 0.02 | 0.06 |
| Hydrogel 3 | 0.52 | 0.12 | 0.54 | 12.6 | 0.05 | 0.09 | 0.04 |
| Hydrogel 4 | 0.94 | 0.81 | 1.24 | 40.5 | 0.10 | 0.19 | 0.13 |
| Hydrogel 5 | 0.11 | 0.54 | 0.55 | 79.0 | N.D. | 0.07 | 0.04 |

Unless defined otherwise, all technical and scientific terms used herein have the same meanings as commonly understood by one of skill in the art to which the disclosed invention belongs. Publications cited herein and the materials for which they are cited are specifically incorporated by reference. Those skilled in the art will recognize, or be able to ascertain using no more than routine experimentation, many equivalents to the specific embodiments of the invention described herein. Such equivalents are intended to be encompassed by the following claim.

We claim:

1. A gel composition comprising nanostructures and formed from a homogenous solution comprising
    a gelator having a molecular weight of 2,500 Da or less,
    one or more local anesthetic agents comprising an ionizable tertiary amine functional group which can exist as an uncharged free base or in a cationic form, and
    a gelation medium comprising water and one or more water-miscible organic solvents comprising dimethylsulfoxide, acetone, dimethylformamide, tetrahydrofuran, dioxane, acetonitrile, or alcohols with a water solubility greater than 5 g/100 g of water,
    wherein the gelation medium comprises between 10 mM and 500 mM of one or more salts when the one or more water-miscible organic solvents comprise dimethylsulfoxide, acetone, dimethylformamide, tetrahydrofuran, dioxane, or acetonitrile,
    wherein the formed gel composition is stable to inversion at room temperature, and
    wherein the one or more local anesthetic agents are encapsulated, entrapped, and/or embedded in the nanostructures of the gel composition via electrostatic interactions between the local anesthetic agents and the gelator of the gel composition, at between about 5% and about 25% by weight in the nanostructures of the gel composition.

2. The gel composition of claim 1, wherein the one or more salts, when present, mediate and/or modify the electrostatic interactions between the local anesthetic agents and the gelator.

3. The gel composition of claim 1, wherein the one or more salts, when present, are selected from the group consisting of sodium chloride, potassium chloride, calcium chloride, magnesium chloride, zinc chloride, monosodium phosphate, and combinations thereof.

4. The gel composition of claim 1, wherein the one or more salts, when present, are present in the gel composition at a concentration between about 15 to about 150 mM.

5. The gel composition of claim 1, wherein the gel composition is dried or lyophilized to remove all solvents.

6. The gel composition of claim 5, wherein the alcohol is selected from the group consisting of methanol, ethanol, isopropanol, t-butanol, and combinations thereof.

7. The gel composition of claim 5, wherein the one or more water-miscible organic solvents are present in the gel composition at a concentration between about 0.1 and 25% volume/volume of total gel.

8. The gel composition of claim 1, wherein the gel has a viscosity between about 0.1 and about 1,000 cP.

9. The gel composition of claim 1, wherein the gel composition formed is a thixotropic gel composition.

10. The gel composition of claim 9, wherein the gel has a G' or G" value of from about 0.1 to about 300 Pa.

11. The gel composition of claim 1, wherein the gel has a shear-dependent viscosity.

12. The gel composition of claim 1, wherein the gelation medium comprises distilled water, de-ionized water, pure or ultrapure water, saline, or other physiologically acceptable aqueous solutions.

13. The gel composition of claim 1, wherein the one or more local anesthetic agents are selected from the group consisting of lidocaine, procaine, tetracaine, dibucaine, bupivacaine, and salts thereof.

14. The gel composition of claim 1, wherein the gelator is selected from:
    an ascorbyl alkanoate selected from the group consisting of ascorbyl palmitate, ascorbyl decanoate ascorbyl laurate, ascorbyl caprylate, ascorbyl myristate, ascorbyl oleate, and combinations thereof;
    a sorbitan alkanoate selected from the group consisting of sorbitan monostearate, sorbitan decanoate, sorbitan laurate, sorbitan caprylate, sorbitan myristate, sorbitan oleate, and combinations thereof;
    a triglycerol monoalkanoate selected from the group consisting of triglycerol monopalmitate, triglycerol monodecanoate, triglycerol monolaurate, triglycerol monocaprylate, triglycerol monomyristate, triglycerol monostearate, triglycerol monooleate, and combinations thereof;
    a sucrose alkanoate selected from the group consisting of sucrose palmitate, sucrose decanoate, sucrose laurate, sucrose caprylate, sucrose myristate, sucrose oleate, and combinations thereof;
    and combinations thereof.

15. The gel composition of claim 1, wherein the gel composition is formed after heating the homogeneous solution and cooling the homogeneous solution to room temperature.

16. The gel composition of claim 1, wherein the gel composition formed is stable to inversion for at least 60 minutes at room temperature.

17. A pharmaceutical formulation comprising the gel composition of claim 1 in a pharmaceutically acceptable carrier,
    optionally wherein the gel composition is in the form of gel particles.

18. A method of forming the self-assembled gel composition of claim 1, comprising:
    preparing a homogenous solution comprising
        a gelator having a molecular weight of 2,500 Da or less and one or more local anesthetic agents comprising an ionizable tertiary amine functional group which can exist as an uncharged free base or in a cationic form in a gelation medium comprising water and one or more water-miscible organic solvents comprising dimethylsulfoxide, acetone, dimethylformamide, tetrahydrofuran, dioxane, acetonitrile, or alcohols with a water solubility greater than 5 g/100 g of water, and between 10 mM and 500 mM of one or more salts when the one or more water-miscible organic solvents comprise dimethylsulfoxide, acetone, dimethylformamide, tetrahydrofuran, dioxane, or acetonitrile;
        and
    permitting the homogenous solution to self-assemble into a self-assembled gel composition;
    wherein the one or more local anesthetic agents are encapsulated, entrapped, and/or embedded in the nanostructures of the self-assembled gel composition via electrostatic interactions between the local anesthetic agents and the gelator of the self-assembled gel composition, at between about 5% and about 25% by weight in the nanostructures of the self-assembled gel composition.

19. The method of claim 18, wherein the one or more salts, when present, are selected from the group consisting of sodium chloride, potassium chloride, calcium chloride, magnesium chloride, zinc chloride, monosodium phosphate, and combinations thereof.

20. The method of claim 18, wherein the one or more local anesthetic agents are selected from the group consisting of lidocaine, procaine, tetracaine, dibucaine, bupivacaine, and salts thereof.

21. The method of claim 18, wherein the gelator is selected from:
   an ascorbyl alkanoate selected from the group consisting of ascorbyl palmitate, ascorbyl decanoate ascorbyl laurate, ascorbyl caprylate, ascorbyl myristate, ascorbyl oleate, and combinations thereof;
   a sorbitan alkanoate selected from the group consisting of sorbitan monostearate, sorbitan decanoate, sorbitan laurate, sorbitan caprylate, sorbitan myristate, sorbitan oleate, and combinations thereof;
   a triglycerol monoalkanoate selected from the group consisting of triglycerol monopalmitate, triglycerol monodecanoate, triglycerol monolaurate, triglycerol monocaprylate, triglycerol monomyristate, triglycerol monostearate, triglycerol monooleate, and combinations thereof;
   a sucrose alkanoate selected from the group consisting of sucrose palmitate, sucrose decanoate, sucrose laurate, sucrose caprylate, sucrose myristate, sucrose oleate, and combinations thereof;
   and combinations thereof.

22. The gel composition of claim 1, wherein the one or more salts, when present, are selected from the group consisting of monosodium phosphate, disodium phosphate, and monopotassium phosphate.

23. The gel composition of claim 1, wherein the gelation medium comprises a phosphate buffered saline at physiological ionic strength.

24. The gel composition of claim 1, comprising at least 4% wt gelator/vol.

25. The gel composition of claim 1, wherein the one or more salts, when present, are present in the gel composition at a concentration between about 20 mM to about 150 mM salt.

26. The gel composition of claim 1, wherein the gel has a viscosity between about 1 and about 400 cP.

27. The gel composition of claim 1, wherein the gel has a viscosity between about 1 and about 10 cP.

28. The method of claim 18, wherein the one or more salts, when present, are selected from the group consisting of monosodium phosphate, disodium phosphate, and monopotassium phosphate.

29. The method of claim 18, wherein the gelation medium comprises a phosphate buffered saline at physiological ionic strength.

* * * * *

UNITED STATES PATENT AND TRADEMARK OFFICE
CERTIFICATE OF CORRECTION

PATENT NO. : 10,881,745 B2
APPLICATION NO. : 15/974535
DATED : January 5, 2021
INVENTOR(S) : Derek G. van der Poll et al.

It is certified that error appears in the above-identified patent and that said Letters Patent is hereby corrected as shown below:

In the Specification

At Column 1, Line 35, please replace "(U.S." with --U.S.--.
At Column 2, Line 63, please replace "wt/%" --wt/wt%--.
At Column 3, Line 37, please replace "post-processing step to tune" with --post-processing step can be used to tune--.
At Column 3, Line 42, please replace "(DMSO), alcohols" with --(DMSO) and alcohols--.
At Column 4, Line 17, please replace "have can have" with --can have--.
At Column 4, Line 28, please replace "gels formed addition" with --gels formed with or without addition--.
At Column 4, Line 56, please replace "Administration)" with --Administration--.
At Column 5, Line 46, please replace "an disorder" with --a disorder--.
At Column 6, Lines 20-21, please replace "spontaneous assemble, or organize, to form a high ordered structure" with --spontaneously assemble, or organize, to form a highly ordered structure--.
At Column 6, Line 52, please replace "sticks to" with --sticking to--.
At Column 9, Line 1, please replace "as wells" with --as well--.
At Column 9, Line 25, please replace "linkage are" with --linkages are--.
At Column 9, Line 54, please replace "at between greater than 0 and 0.15 M" with --at, between or greater than 0 and 0.15 M--.
At Column 10, Line 19, please replace "wt/%" --wt/wt%--.
At Column 10, Lines 59-60, please replace "about 0.1 to about 300 mM, about 0.1 to about 300 mM" with --about 0.1 to about 300 mM--.
At Column 11, Line 21, please replace "(DMSO), alcohols" with --(DMSO) and alcohols--.
At Column 11, Line 49, please replace "process" with --processed--.
At Column 11, Line 58, please replace "Administration)" with --Administration--.
At Column 13, Line 55, please replace "forms gel" with --forms a gel--.
At Column 13, Line 63, please replace "forms gel" with --forms a gel--.
At Column 18, Line 34, please replace "at between greater than 0 and 0.15 M" with --at, between or greater than 0 and 0.15 M--.
At Column 18, Line 66, please replace "wt/%" --wt/wt%--.

Signed and Sealed this
First Day of November, 2022

Katherine Kelly Vidal
*Director of the United States Patent and Trademark Office*

CERTIFICATE OF CORRECTION (continued)
U.S. Pat. No. 10,881,745 B2

At Column 19, Lines 39-40, please replace "about 0.1 to about 300 mM, about 0.1 to about 300 mM" with --about 0.1 to about 300 mM--.
At Column 19, Line 62, please replace "post-processing step to tune" with --post-processing step can be used to tune--.
At Column 19, Line 67, please replace "(DMSO), alcohols" with --(DMSO) and alcohols--.
At Column 20, Line 55, please replace "have can have" with --can have--.
At Column 20, Line 66, please replace "gels formed addition" with --gels formed with or without addition--.
At Column 21, Line 27, please replace "Administration)" with --Administration--.
At Column 22, Line 3, please replace "longer)" with --longer--.
At Column 23, Line 37, please replace "Pharmaceutical carrier" with --Pharmaceutical carriers--.
At Column 23, Line 58, please replace "the intravenous administration, or injected directly" with --intravenous administration, or injection directly--.
At Column 23, Line 65, please replace "techniques is known" with --techniques known--.
At Column 24, Line 22, please replace "procession" with --processing--.
At Column 24, Line 43, please replace "stomach" with --stomach.--.
At Column 25, Lines 64-65, please replace "about 0.1 to about 300 mM, about 0.1 to about 300 mM" with --about 0.1 to about 300 mM--.
At Column 26, Line 30, please replace "(DMSO), alcohols" with --(DMSO) and alcohols--.
At Column 27, Line 19, please replace "gels formed addition" with --gels formed with or without addition--.
At Column 29, Line 59, please replace "agents is" with --agents are--.
At Column 30, Line 47, please replace "bacterial conditions, viral conditions" with --bacterial conditions, and viral conditions--.
At Column 33, Lines 56-57, please replace "the gels suspensions" with --the gel suspensions--.
At Column 34, Line 12, please replace "lead to" with --leads to--.

In the Claims

In Claim 14, Column 40, Lines 12-13, please replace "ascorbyl decanoate ascorbyl laurate" with --ascorbyl decanoate, ascorbyl laurate--.
In Claim 21, Column 41, Lines 17-18, please replace "ascorbyl decanoate ascorbyl laurate" with --ascorbyl decanoate, ascorbyl laurate--.